US007790204B2

(12) United States Patent
Dewhirst et al.

(10) Patent No.: US 7,790,204 B2
(45) Date of Patent: *Sep. 7, 2010

(54) USE OF AN AGENT THAT RESTORES TISSUE PERFUSION AND OXYGENATION

(75) Inventors: Mark W. Dewhirst, Durham, NC (US); Jonathan S. Stamler, Chapel Hill, NC (US); Timothy J. McMahon, Durham, NC (US); Pierre Sonveaux, Ottignies-Louvain-la-Neuve (BE)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/006,842

(22) Filed: Jan. 7, 2008

(65) Prior Publication Data

US 2008/0107637 A1 May 8, 2008

Related U.S. Application Data

(63) Continuation of application No. 11/404,494, filed on Apr. 13, 2006, now Pat. No. 7,338,670.

(60) Provisional application No. 60/671,179, filed on Apr. 14, 2005.

(51) Int. Cl.
*A61K 9/00* (2006.01)
*A61K 38/00* (2006.01)

(52) U.S. Cl. .......................................... 424/700; 514/12

(58) Field of Classification Search ................. 514/788, 514/12

See application file for complete search history.

(56) References Cited

U.S. PATENT DOCUMENTS

| | | | |
|---|---|---|---|
| 5,405,940 A | 4/1995 | Boon et al. | |
| 5,462,871 A | 10/1995 | Boon-Falleur et al. | |
| 5,695,994 A | 12/1997 | Boon-Falleur et al. | |
| 6,034,214 A | 3/2000 | Boon et al. | |
| 6,222,012 B1 | 4/2001 | Boon-Falleur et al. | |
| 6,314,956 B1 | 11/2001 | Stamler et al. | |
| 6,379,901 B1 | 4/2002 | Boon-Falleur et al. | |
| 6,488,932 B1 | 12/2002 | Boon et al. | |
| 6,676,855 B2 | 1/2004 | Stamler | |
| 6,945,247 B1 | 9/2005 | Stamler et al. | |
| 7,338,670 B2 | 3/2008 | Dewhirst et al. | |
| 2002/0037839 A1* | 3/2002 | Stamler et al. ................ | 514/6 |
| 2006/0276374 A1 | 12/2006 | Dewhirst et al. | |

2008/0113901 A1 5/2008 Dewhirst et al.

FOREIGN PATENT DOCUMENTS

| | | |
|---|---|---|
| WO | WO94/05304 | 3/1994 |
| WO | WO94/16713 | 8/1994 |
| WO | WO95/25530 | 9/1995 |
| WO | WO95/33855 | 12/1995 |
| WO | WO96/29409 | 9/1996 |
| WO | WO98/32855 | 7/1998 |
| WO | WO98/58956 | 12/1998 |

OTHER PUBLICATIONS

Braun et al., Fourier analysis of fluctuations of oxygen tension and blood flow in R3230Ac tumors and muscle in rats. *American Journal of Physiology*. vol. 277 pp. H551-H568 (1999).
Chaux et al., Identification of five MAGE-A1 epitopes recognized by cytolytic T lymphocytes obtained by in vitro stimulation with dendritic cells transduced with MAGE-A1. *Journal of Immunology*. vol. 163 pp. 2928-2936 (1999).
Comerford et al., Hypocia-inducible factor-1-dependent regulation of the Multidrug Resistance gene (MDRG). *Cancer Research*. vol. 62 pp. 3387-3394 (2002).
Dachs et al., Hypoxia modulated gene expression: angiogenesis, metastasis and therapeutic exploitation. *European Journal of Cancer*. vol. 36 pp. 1649-1660 (2000).
Dewhirst et al., Arteriolar oxygenation in tumor and subcutaneous arterioles: effects of inspired air oxygen content. *British Journal of Cancer*. vol. 74 pp. S241-S246 (1996).

(Continued)

*Primary Examiner*—Maryam Monshipouri
(74) *Attorney, Agent, or Firm*—Jenkins, Wilson, Taylor & Hunt, P.A.

(57) ABSTRACT

The presently disclosed subject matter provides methods for increasing perfusion in hypoxic regions of tissues in subjects. Also provided are methods for treating diseases and/or disorders associated with hypoxia in subjects, methods for increasing sensitivity of tumors to radiation and/or chemotherapy treatments, methods for delaying tumor growth in subjects, and methods for inhibiting tumor blood vessel growth in subjects. In some embodiments, the presently disclosed methods involve administering to subjects in need thereof a first composition selected from the group consisting of a nitrosylated hemoglobin and an agent that induces nitrosylation of endogenous hemoglobin in the subject and a second composition comprising a hyperoxic gas. In some embodiments, the presently disclosed methods also include treating a tumor with radiation therapy, chemotherapy, photodynamic therapy, immunotherapy, or combinations thereof. Also provided are inhalable gases that can be employed in the presently disclosed methods.

11 Claims, 9 Drawing Sheets

OTHER PUBLICATIONS

Dewhirst et al., Quantification of longitudinal tissue pO2 gradients in window chamber tumours: impact on tumour hypoxia. *British Journal of Cancer*. vol. 79 pp. 1717-1722 (1999).

Dolmans et al., Photodynamic therapy for cancer. *Nature*. vol. 3 pp. 380-387 (2003).

Gaugler et al., Human gene MAGE-3 codes for an antigen recognized on a melanoma by autologous cytolytic T lymphocytes. *Journal of Experimental Medicine*. vol. 179 pp. 921-930 (1994).

Godelaine et al., Polyclonal CTL responses observed in melanoma patients vaccinated with dendritic cells pulsed with a MAGE-3.A1 peptide. *The Journal of Immunology*. vol. 171 pp. 4893-4897 (2003).

Goldstein, L.J., MDR1 gene expression in solid tumours. *European Journal of Cancer*. vol. 32A, No. 6 pp. 1039-1050 (1996).

Hill et al., Microregional blood flow in murine and human tumours assessed using laser Doppler microprobes. *British Journal of Cancer*. vol. 74 pp. S260-S263 (1996).

Kimura et al., Fluctuations in red cell flux in tumor microvessels can lead to transient hypoxia and reoxygenation in tumor parenchyma. *Cancer Research*. vol. 56 pp. 5522-5528 (1996).

Kinoshita et al., Cancer cells surviving hypoxia obtain hypoxia resistance and maintain anti-apoptotic potential under reoxygenation. *International Journal of Cancer*. vol. 91 pp. 322-326 (2001).

Le et al., Nitric oxide synthase II suppresses the growth and metastasis of human cancer regardless of its up-regulation of protumor factors. *Proceedings of the National Academy of Sciences of USA*. vol. 102 pp. 8758-8763 (2005).

Lewis et al., Macrophage responses to hypoxia. Implications for tumor progression and anti-cancer therapies. *American Journal of Pathology*. vol. 167, No. 3 pp. 627-635 (2005).

Moeller et al., Pleiotropic effects if HIF-1 blockade on tumor radiosensitivity. *Cancer Cell*. vol. 8 pp. 99-110 (2005).

Notice of Allowance corresponding to U.S. Appl. No. 11/404,494 dated Oct. 18, 2007.

Notice of Allowance corresponding to U.S. Appl. No. 12/006,849 dated Jul. 13, 2009.

Official Action corresponding to U.S. Appl. No. 11/404,494 dated Mar. 2, 2007.

Official Action corresponding to U.S. Appl. No. 12/006,849 dated Jul. 24, 2008.

Official Action corresponding to U.S. Appl. No. 12/006,849 dated Jan. 26, 2009.

Teicher at al., Classification of antineoplastic agents by their selective toxicities toward oxygenated and hypoxic tumor cells. *Cancer Research*. vol. 41 pp. 73-81 (1981).

Teicher et al., Differenttial enhancement of melphalan cytotoxicity in tumor and normal tissue by Fluosol-DA.RTM. and oxygen breathing. *International Journal of Cancer*. vol. 36 pp. 585-589 (1995).

Tsai et al., Evidence of flowmotion induced changes in local tissue oxygenation. *International Journal of Microcirculation: Clinical Experiment*. vol. 12 pp. 75-88 (1993).

Van Baren et al., Tumoral and immunologic response after vaccination of melanoma patients with an ALVAC virus encoding MAGE antigens recognized by T cells. *Journal of Clinical Oncology*. vol. 23, No. 35 pp. 9008-9021 (2005).

Van den Eynde et al., A new family of genes coding for an antigen recognized by autologous cytolytic T lymphocytes on a human melanoma. *Journal of Experimental Medicine*. vol. 182 pp. 689-698 (1995).

Vaupel et al., Oxygenation status of malignant tumors: pathogenesis of hypoxia and significance for tumor therapy. *Seminars in Oncology*. vol. 28, No. 2, Suppl. 8 pp. 29-35 (2001).

Notification of Transmittal of the International Search Report and the Written Opinion of the International Searching Authority, or the Declaration corresponding to International Application No. PCT/US06/14257 dated Jun. 16, 2008.

Stamler et al., Blood Flow Regulation by S-Nitrosohemoglobin in the Physiological Oxygen Gradient. *Science*. vol. 276 pp. 2034-2036 (1997).

Brizel et al., "The Mechanisms by Which hyperbaric oxygen and carbogen improve tumour oxygenation," *British Journal of Cancer*, vol. 72, pp. 1120-1124 (1995).

Dunn et al., "The effects of hyperoxic and hypercarbic gases on tumour blood flow," Br. J. Cancer., vol. 80, pp. 117-126 (1999).

Hardee et al., "Novel Imaging Provides New Insights into Mechanism of Oxygen Transport in Tumors," Current Molecular Medicine, vol. 9, pp. 435-441 (2009).

Secomb et al., "Analysis of the Effects of Oxygen Supply and Demand on Hypoxic Fraction in Tumors," Acta Oncologica, vol. 34, pp. 313-316 (1995).

Ali et al., "A method to attenuate pneumoperitoneum-induced reductions in splanchnic blood flow," Ann. Surg., vol. 241, pp. 256-261 (2005).

Baumann et al., "Response of human squamous cell carcinoma xenografts of different sizes to irradiation: relationship of clonogenic cells, cellular radiation sensitivity in vivo, and tumor rescuing units," Radiat. Res., vol. 123, pp. 325-330 (1990).

Bingle et al., "The role of tumour-associated macrophages in tumour progression: implications for new anticancer therapies," J. Pathol., vol. 196, pp. 254-265 (2002).

Boon et al., "Tumor antigens recognized by T lymphocytes," Annual Rev. Immunol., vol. 12, pp. 337-365 (1994).

Churchill-Davidson et al., "High pressure oxygen and radiotherapy," Lancet, vol. 1, pp. 1091-1095 (1955).

Dejam et al., "Erythrocytes are the major intravascular storage sites of nitrite in human blood," Blood, vol. 106, pp. 734-739 (2005).

Dische,S., "A review of hypoxic cell radiosensitization," Int. J. Radiat. Oncol. Biol. Phys., vol. 20, pp. 147-152 (1991).

Ferranti et al., "Characterisation of S-nitrosohaemoglobin by mass spectrometry," FEBS Lett., vol. 400, pp. 19-24 (1997).

Fukumura et al., "Role of nitric oxide in tumor microcirculation. Blood flow, vascular permeability, and leukocyte-endothelial interactions," Am. J. Pathol., vol. 150, pp. 713-725 (1997).

Gaston, B., "Nitric oxide and thiol groups," Biochim. Biophys. Acta, vol. 1411, pp. 323-333 (1999).

Gaston et al., "The biology of nitrogen oxides in the airways," Am. J. Respir. Crit. Care Med., vol. 149, pp. 538-551 (1994).

Goldstein, L. J., "MDR1 gene expression in solid tumours," Eur. J. Cancer, vol. 32A, pp. 1039-1050 (1996).

Griffin et al., "Radiosensitization of hypoxic tumor cells in vitro by nitric oxide," Int. J. Radiat. Oncol. Biol. Phys., vol. 36, pp. 377-383 (1996).

Griffin et al., "Radiosensitization of two murine tumours with mild temperature hyperthermia and carbogen breathing," Int. J. Radiat. Biol., vol. 75, pp. 1299-1306 (1999).

Hamilton et al., "The glutathione system in alkylator resistance," Cancer Treat. Res., vol. 112, pp. 67-87 (2002).

Hilf et al., "Biochemical and Morphologic Properties of a New Lactating Mammary Tumor Line in the Rat," Cancer Res., vol. 25, pp. 286-299 (1965).

Interview Summary corresponding to U.S. Appl. No. 12/006,849 dated Aug. 31, 2009.

Janssens et al., "Activation of inducible nitric oxide synthase results in nitric oxide-mediated radiosensitization of hypoxic EMT-6 tumor cells," Cancer Res., vol. 58, pp. 5646-5648 (1998).

Janssens et al., "Radiosensitization of hypoxic tumour cells by S-nitroso-N-acetylpenicillamine implicates a bioreductive mechanism of nitric oxide generation," Br. J. Cancer, vol. 79, pp. 1085-1089 (1999).

Jordan et al., "Potentiation of radiation-induced regrowth delay by isosorbide dinitrate in FSaII murine tumors," Int. J. Cancer, vol. 103, pp. 138-141 (2003).

Jordan et al., "Nitric oxide as a radiosensitizer: evidence for an intrinsic role in addition to its effect on oxygen delivery and consumption," Int. J. Cancer (2004). In Press.

Kaanders et al., "ARCON: a novel biology-based approach in radiotherapy," Lancet Oncol., vol. 3, pp. 728-737 (2002).

Kagan et al., "Pro-oxidant and Antioxidant Mechanisms of Etoposide in HL-60 Cells," Cancer Res., vol. 61, pp. 7777-7784 (2001).

Masunaga et al., "Enhancement of chemosensitivity of quiescent cell populations in murine solid tumors using nicotinamide," Chemotherapy, vol. 40, pp. 418-426 (1994).

McMahon & Stamler, "Concerted nitric oxide/oxygen delivery by hemoglobin," Methods Enzymol., vol. 301, pp. 99-114 (1999).

McMahon et al., "Nitric oxide in the human respiratory cycle," Nat. Med., vol. 8, pp. 711-717 (2002).

Mitchell et al., Radiation sensitisation by nitric oxide releasing agents, Br. J. Cancer, Suppl. 27, pp. S181-S184 (1996).

Mitchell et al., "Redox generation of nitric oxide to radiosensitize hypoxic cells," Int. J. Radiat. Oncol. Biol. Phys., vol. 42, pp. 795-798 (1998).

Moya et al., "Inhaled ethyl nitrite gas for persistent pulmonary hypertension of the newborn," Lancet, vol. 360, pp. 141-143 (2002).

Moya et al., "S-nitrosothiol repletion by an inhaled gas regulates pulmonary function," Proc. Natl. Acad. Sci. U. S. A., vol. 98, pp. 5792-5797 (2001).

Mueller-Klieser et al., "Tumour oxygenation under normobaric and hyperbaric conditions," Br. J. Radiol., vol. 56, pp. 559-564 (1983).

Murdoch et al., "Mechanisms regulating the recruitment of macrophages into hypoxic areas of tumors and other ischemic tissues," Blood, vol. 104, No. 8, pp. 2224-2234 (Oct. 15, 2004).

Notice of Allowance corresponding to U.S. Appl. No. 11/404,494 dated Dec. 7, 2007.

Office Communication corresponding to U.S. Appl. No. 12/006,849 dated Nov. 19, 2009.

Peeters et al., "Vascular density in colorectal liver metastases increases after removal of the primary tumor in human cancer patients," Int. J. Cancer, vol. 112, pp. 554-559 (2004).

Rassaf et al., "Evidence for in vivo transport of bioactive nitric oxide in human plasma," J. Clin. Invest., vol. 109, pp. 1241-1248 (2002).

Richardson et al., "Potential therapeutic uses for S-nitrosothiols," Clin. Sci. (Lond.), vol. 102, pp. 99-105 (2002).

Rojas, A., "Radiosensitization with normobaric oxygen and carbogen," Radiother. Oncol., vol. 20, Suppl. 1, pp. 65-70 (1991).

Scharfstein et al., "In vivo transfer of nitric oxide between a plasma protein-bound reservoir and low molecular weight thiols," J. Clin. Invest., vol. 94, pp. 1432-1439 (1994).

Shan et al., "Effects of diethylamine/nitric oxide on blood perfusion and oxygenation in the R3230Ac mammary carcinoma," Br. J. Cancer, vol. 76, pp. 429-437 (1997).

Sorg et al., "Hyperspectral imaging of hemoglobin saturation in tumor microvasculature and tumor hypoxia development," J. Biomed. Opt., vol. 10, p. 44004 (2005).

Thews et al., "No improvement in perfusion and oxygenation of experimental tumors upon application of vasodilator drugs," Int. J. Oncol., vol. 19, pp. 1243-1247 (2001).

Traversari et al., "A Nonapeptide Encoded by Human Gene MAGE-1 Is Recognized on HLAA1 by Cytolytic T Lymphocytes Directed against Tumor Antigen MZ2-E," J. Exp. Med., vol. 176, pp. 1453-1457 (1992).

van der Bruggen et al., "Autologous cytolytic T lymphocytes recognize a MAGE-1 nonapeptide on melanomas expressing HLA-Cw* 1601," Eur. J. Immunol., vol. 24, pp. 2134-2140 (1994).

van der Sanden et al., "Effect of carbogen breathing on the physiological profile of human glioma xenografts," Magn. Reson. Med., vol. 42, pp. 490-499 (1999).

Wood et al., "Changes in energy metabolism and X-ray sensitivity in murine tumours by the nitric oxide donor SIN-1," Br. J. Cancer, Suppl. 27, pp. S177-S180 (1996).

Wood et al., "Modification of energy metabolism and radiation response of a murine tumour by changes in nitric oxide availability," Biochem. Biophys. Res. Commun., vol. 192, pp. 505-510 (1993).

Yaromina et al., "Does heterogeneity of pimonidazole labelling correspond to the heterogeneity of radiation-response of FaDu human squamous cell carcinoma?" Radiother. Oncol., vol. 76, pp. 206-212 (2005).

Zhong et al., "Overexpression of Hypoxia-inducible Factor 1 in Common Human Cancers and Their Metastases," Cancer Res., vol. 59, pp. 5830-5835 (1999).

* cited by examiner

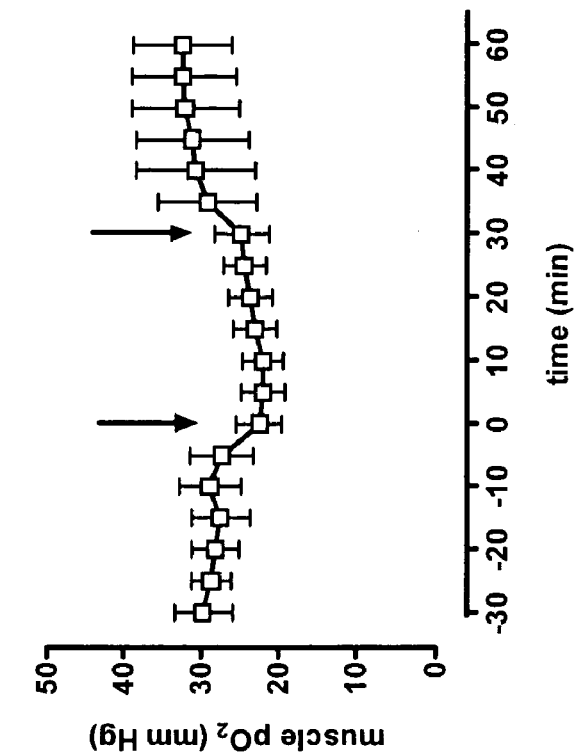
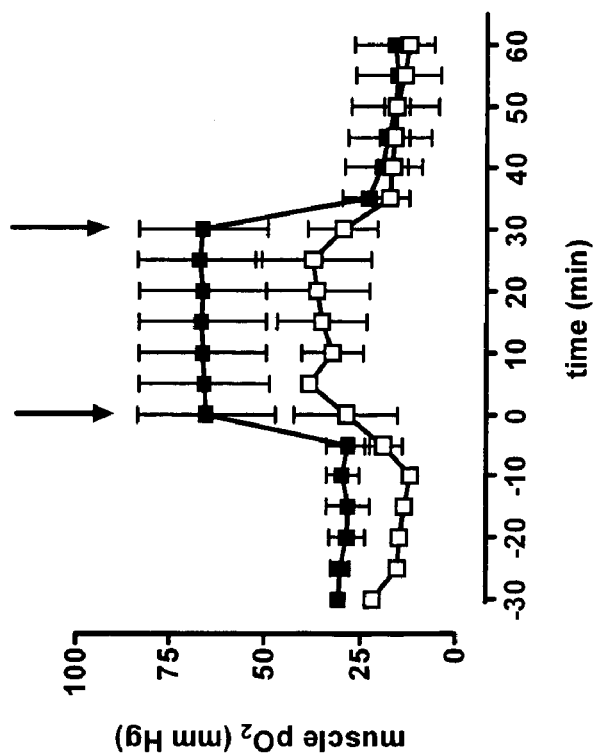
FIGURE 6A
FIGURE 6B

USE OF AN AGENT THAT RESTORES TISSUE PERFUSION AND OXYGENATION

RELATED APPLICATIONS

This application is a continuation of U.S. patent application Ser. No. 11/404,494, filed Apr. 13, 2006, now U.S. Pat. No. 7,338,670, which itself claims the benefit of U.S. Provisional Patent Application Ser. No. 60/671,179, filed Apr. 14, 2005; the disclosure of each of which is incorporated herein by reference in its entirety.

GOVERNMENT INTEREST

The presently disclosed subject matter was made with United States Government support under Grant No. CA40355 awarded by the National Institutes of Health/National Cancer Institute. Thus, the U.S. Government has certain rights in the presently disclosed subject matter.

TECHNICAL FIELD

The presently disclosed subject matter provides methods for increasing perfusion in hypoxic regions of tissues in subjects. Also provided are methods for treating diseases and/or disorders associated with hypoxia in subjects, methods for increasing sensitivity of tumors to radiation and/or chemotherapy treatments, and/or other circulating antitumor treatments, diagnostic agents, and/or prognostic agents, methods for delaying tumor growth in subjects, and methods for inhibiting tumor blood vessel growth in subjects. Also provided are compositions that can be employed in the presently disclosed methods.

BACKGROUND

Hypoxia (a reduction in the normal level of oxygen tension) is a common feature of both experimental and human solid tumors. It results from an imbalance between oxygen supply and consumption (Dachs & Tozer, 2000). This fundamental characteristic of tumor cells is of major clinical importance since hypoxia can predict both tumor progression and poor treatment outcome (Dachs & Tozer, 2000; Vaupel et al., 2001).

Diffusion-limited hypoxia is generally believed to arise from the increasing metabolic demands of the growing mass of cells at increasing intercapillary distances. However, there is now clear evidence that this might not be the only determinant of chronic hypoxia. Another cause is of hypoxia relates to the level of oxygenation of the incoming blood. Indeed, before entering a tumor, a continuous diffusion of oxygen between the blood and the interstitium along the vascular tree accounts for an estimated two-thirds hemoglobin (Hb) deoxygenation (Pittman, 1995). Then, in order for blood to reach the tumor periphery, it must first pass through moderately hypoxic tissues where most of the remaining oxygen in the blood is extracted (Dewhirst et al., 1999).

As a result of this steep vascular gradient of hemoglobin desaturation, many vessels in tumors carry severely deoxygenated blood, so their ability to supply oxygen to the tumor is limited. Additional regions of severe hypoxia in solid tumors result from the uneven partition of erythrocytes in the tumor microvasculature, leading to measurable changes in vascular and perivascular $PO_2$ (fluctuant hypoxia; Dewhirst et al., 1996; Kimura et al., 1996; Hill et al., 1996). Low-frequency red cell flux and $pO_2$ fluctuations in tumors are of high magnitude, which results in a decrease in average tissue oxygenation and a greater variability in local tissue $pO_2$ (Braun et al., 1999; Kimura et al., 1996; Tsai & Intaglietta, 1993). Fluctuating arteriolar diameter might also contribute to flow instability in tumor microvessels (Dewhirst et al., 1996). This, along with the tortuous tumor vasculature accounting for unstable vascular pressures, results in very unstable blood flow, unstable and heterogeneous oxygenation, and areas of fluctuant hypoxia in tumors. Local tumor $pO_2$ can often transiently drop below 3-10 mm Hg (Kimura et al., 1996; Braun et al., 1999), which is considered to be the critical $pO_2$ for radiosensitization (radiobiological hypoxia).

Thus, radiological treatment of tumors is often met with limited success due at least in part to a sub-optimal concentration of oxygen in the tumors. In biological systems, irradiation induces water radiolysis and the subsequent production of the highly reactive reactive oxygen species ($OH^-$, $O_2^-$, and $H_2O_2$; Mundt et al., 2000). Their most important reactions with biological structures, in terms of therapeutic effect, are those involving DNA, because they are more likely to impair cell survival. They lead to the reversible formation of DNA radicals, which can lead to strand breaks. However, if oxygen is present, then it can react with DNA to produce DNA-$O_2$·, which then undergoes further reaction to ultimately yield DNA-OOH (Horsman & Overgaard, 2002). Oxygen-dependent fixation of DNA damage is known as the 'oxygen effect'. It accounts for the high radiosensitivity of oxygenated areas in tumors; by contrast, hypoxic areas are less sensitive. Upon base damage, DNA reorganization can result in intra- or inter-strand crosslinking, crosslinks between DNA and chromosomal proteins, and single or double DNA strand breaks (McMillan & Steel, 2002). As a consequence, radiation-induced damage is primarily manifested by the loss of cellular reproductive integrity.

Many chemotherapeutic agents are also dependent on cellular oxygenation for maximal efficacy. Cytotoxic alkylating agents, such as the nitrogen mustard alkylating agent melphalan, comprise a class of chemotherapeutic drugs that act by transferring alkyl groups to DNA during cell division. Following this, the DNA strand breaks or cross-linking of the two strands occurs, preventing subsequent DNA synthesis. In a study by Teicher et al., tumor cells in normoxic conditions were more sensitive to melphalan, in contrast to their hypoxic counterparts (Teicher et al., 1985). Under hypoxic conditions, alkylating agents might have less efficacy due to the increased production of nucleophilic substances such as glutathione that can compete with the target DNA for alkylation (Hamilton et al., 2002).

Other examples of drugs directly effected by a lack of $O_2$ include the antibiotic bleomycin and the podophyllotoxin derivative etoposide. Bleomycin does not have maximum efficacy due to the reduced generation of free radicals under hypoxic conditions (Teicher et al., 1981). Etoposide efficacy is reduced due to free radical scavengers, dehydrogenase inhibitors, and dehydrogenase substrates, which prevent the formation of single-strand breaks, thereby decreasing the cytotoxic effects of etoposide (Kagan et al., 2001).

Anticancer drugs such as alkylating agents and antimetabolites act mainly during DNA synthesis by causing damage to the DNA and initiating apoptosis. These drugs can therefore have reduced efficacy on slowly cycling tumor cells under hypoxic conditions. DNA-damaging chemotherapeutic agents such as alkylating agents and platinum compounds might also have compromised function due to increased activity of DNA repair enzymes under hypoxic conditions. Hypoxia also increases the production of various proteins that appear to be responsible for drug resistance (Goldstein, 1996; Zhong et al., 1999; Kinoshita et al., 2001; Comerford et al., 2002).

What are needed, then, are new methods and compositions that can be employed for reducing and/or eliminating hypoxic regions of tumors and other cells that are generally treated with therapies that require the presence of oxygen to be maximally effective. The presently disclosed subject matter addresses this and other needs in the art.

SUMMARY

The presently disclosed subject matter provides methods of increasing perfusion in a hypoxic region of a tissue in a subject. In some embodiments, the methods comprise administering to the subject (a) a composition selected from the group consisting of (i) a nitrosylated hemoglobin; (ii) an agent that induces nitrosylation of hemoglobin in the subject; (iii) a hemoglobin and an agent that induces nitrosylation of hemoglobin in the subject; and (iv) combinations thereof; and (b) a hyperoxic gas. In some embodiments, the agent that induces nitrosylation of hemoglobin in the subject comprises ethyl nitrite (ENO). In some embodiments, the ethyl nitrite (ENO) is administered to the subject as an inhalable composition comprising about 100 parts per million (ppm) in the hyperoxic gas. In some embodiments, the hemoglobin is present within a red blood cell. In some embodiments, the red blood cell is present within the subject. In some embodiments, the hemoglobin is present within a red blood cell that is administered to the subject. In some embodiments, the hyperoxic gas is selected from the group consisting of pure oxygen and carbogen. In some embodiments, the tissue comprises a tumor cell, a cancer cell, and combinations thereof. In some embodiments, the subject is a mammal. In some embodiments, the mammal is a human. In some embodiments, the administering results increases a $pO_2$ value in at least a fraction of the hypoxic region of the tissue to at least about 10 mm Hg. In some embodiments, the hypoxic region of the tissue results from a disease or disorder in the subject, and the administering ameliorates at least one symptom associated with the disease or disorder in the subject.

The presently disclosed subject matter also provides methods for treating a disease or disorder associated with hypoxia in a subject. In some embodiments, the methods comprise administering to the subject (a) a composition selected from the group consisting of a nitrosylated hemoglobin, an agent that induces nitrosylation of hemoglobin in the subject, a hemoglobin and an agent that induces nitrosylation of hemoglobin in the subject, and combinations thereof; and (b) a hyperoxic gas. In some embodiments, the agent that induces nitrosylation of endogenous hemoglobin in the subject comprises ethyl nitrite (ENO). In some embodiments, the ethyl nitrite (ENO) is administered to the subject at about 100 parts per million (ppm) in the hyperoxic gas. In some embodiments, the hemoglobin is present within a red blood cell. In some embodiments, the red blood cell is present within the subject. In some embodiments, the hemoglobin is present within a red blood cell that is administered to the subject. In some embodiments, the hyperoxic gas is selected from the group consisting of pure oxygen and carbogen. In some embodiments, the disease or disorder comprises a tumor, a cancer, peripheral vascular disease, diabetes, a disease related to smoking, cirrhosis, rheumatoid arthritis, stroke, myocardial infarction, and combinations thereof. In some embodiments, the disease or disorder comprises a tumor, a cancer, or combinations thereof, and the methods further comprise treating the subject with a second therapy selected from the group consisting of radiotherapy, chemotherapy, immunotherapy, surgery, photodynamic therapy, and combinations thereof. In some embodiments, the treating the subject with a second therapy step is performed concurrently with the administering step. In some embodiments, the subject is a mammal. In some embodiments, the mammal is a human. In some embodiments, the administering results increases a $pO_2$ value in at least a fraction of the hypoxic region of the tissue to at least about 10 mm Hg.

The presently disclosed subject matter also provides methods for increasing a sensitivity of a tumor in a subject to a treatment. In some embodiments, the methods comprise administering to the subject (a) a composition selected from the group consisting of a nitrosylated hemoglobin, an agent that induces nitrosylation of hemoglobin in the subject, a hemoglobin and an agent that induces nitrosylation of hemoglobin in the subject, and combinations thereof; and (b) a hyperoxic gas, wherein the administering increases $pO_2$ in a plurality of cells of the tumor to above about 10 mm Hg, thereby increasing sensitivity of the tumor to the treatment. In some embodiments, the treatment is selected from the group consisting of radiotherapy, chemotherapy, photodynamic therapy, immunotherapy, and combinations thereof. In some embodiments, the agent that induces nitrosylation of endogenous hemoglobin in the subject comprises ethyl nitrite (ENO). In some embodiments, the ethyl nitrite (ENO) is administered to the subject as an inhalable composition comprising about 100 parts per million (ppm) in the hyperoxic gas. In some embodiments, the administering comprises administering a minimally therapeutic dose of the first composition and the second composition. In some embodiments, the tumor is resistant to radiation therapy, chemotherapy, or both radiation therapy and chemotherapy. In some embodiments, the hemoglobin is present within a red blood cell. In some embodiments, the red blood cell is present within the subject. In some embodiments, the hemoglobin is present within a red blood cell that is administered to the subject. In some embodiments, the subject is a mammal. In some embodiments, the mammal is a human.

The presently disclosed subject matter also provides methods for delaying tumor growth in a subject. In some embodiments, the methods comprise (a) administering to the subject (i) a composition selected from the group consisting of a nitrosylated hemoglobin, an agent that induces nitrosylation of hemoglobin in the subject, a hemoglobin and an agent that induces nitrosylation of hemoglobin in the subject, and combinations thereof; and (ii) a hyperoxic gas, wherein the administering increases $pO_2$ in a plurality of cells of the tumor to above about 10 mm Hg; and (b) treating the tumor with radiation therapy, chemotherapy, or both radiation therapy and chemotherapy, whereby tumor growth in the subject is delayed. In some embodiments, the tumor is resistant to radiation therapy, chemotherapy, or both radiation therapy and chemotherapy. In some embodiments, the agent that induces nitrosylation of endogenous hemoglobin in the subject comprises ethyl nitrite (ENO). In some embodiments, the ethyl nitrite (ENO) is administered to the subject as an inhalable composition comprising about 100 parts per million (ppm) in the hyperoxic gas. In some embodiments, the hemoglobin is present within a red blood cell. In some embodiments, the red blood cell is present within the subject. In some embodiments, the hemoglobin is present within a red blood cell that is administered to the subject. In some embodiments, the subject is a mammal. In some embodiments, the mammal is a human. In some embodiments, the treating the tumor with radiation therapy comprises treating the tumor with a subtherapeutic dose of ionizing radiation. In some embodiments, the treating the tumor with chemotherapy comprises administering to the subject a therapeutically effective amount of a chemotherapy agent. In some embodiments, the methods further comprise promoting tumor regression.

The presently disclosed subject matter also provides methods for inhibiting tumor blood vessel growth in a subject. In some embodiments, the methods comprise (a) administering to the subject (i) a composition selected from the group consisting of a nitrosylated hemoglobin, an agent that induces nitrosylation of hemoglobin in the subject, a hemoglobin and an agent that induces nitrosylation of hemoglobin in the subject, and combinations thereof; and (ii) a hyperoxic gas, wherein the administering increases pO2 in a plurality of cells of the tumor to above about 10 mm Hg; and (b) treating the tumor with radiation therapy, chemotherapy, or both radiation therapy and chemotherapy, whereby tumor blood vessel growth in the subject is inhibited. In some embodiments, the agent that induces nitrosylation of hemoglobin in the subject comprises ethyl nitrite (ENO). In some embodiments, the ethyl nitrite (ENO) is administered to the subject as an inhalable composition comprising about 100 parts per million (ppm) in the hyperoxic gas. In some embodiments, the hemoglobin is present within a red blood cell. In some embodiments, the red blood cell is present within the subject. In some embodiments, the hemoglobin is present within a red blood cell that is administered to the subject. In some embodiments, the subject is a mammal. In some embodiments, the mammal is a human. In some embodiments, the methods further comprise delaying tumor growth in the subject. In some embodiments, the methods further comprise promoting tumor regression in the subject.

The presently disclosed subject matter also provides methods of enhancing delivery of a diagnostic, therapeutic, or prognostic agent to a tumor in a subject. In some embodiments, the methods comprise (a) administering to the subject a composition selected from the group consisting of a nitrosylated hemoglobin, a nitrosylating agent that induces nitrosylation of hemoglobin in the subject, a hemoglobin and a nitrosylating agent that induces nitrosylation of hemoglobin in the subject, and combinations thereof; and (b) administering a diagnostic, therapeutic, or prognostic agent to the subject, wherein delivery of the diagnostic, therapeutic, or prognostic agent to a tumor in the subject is enhanced. In some embodiments, the composition comprises the diagnostic, therapeutic, or prognostic agent. In some embodiments, the diagnostic, therapeutic, or prognostic agent comprises an imaging agent. In some embodiments, the methods further comprise administering to the subject a hyperoxic gas selected from the group consisting of 100% oxygen and carbogen. In some embodiments, the subject is a mammal. In some embodiments, the mammal is a human.

The presently disclosed subject matter also provides inhalable compositions. In some embodiments, the inhalable compositions comprise (a) a composition selected from the group consisting of a nitrosylated hemoglobin, an agent that induces nitrosylation of hemoglobin in the subject, a hemoglobin and an agent that induces nitrosylation of hemoglobin in the subject, and combinations thereof; and (b) a hyperoxic gas. In some embodiments, the inhalable composition comprises at least about 100 parts per million (ppm) ethyl nitrite (ENO). In some embodiments, the hyperoxic gas is selected from the group consisting of pure oxygen and carbogen.

Accordingly, it is an object of the presently disclosed subject matter to provide methods and compositions for increasing perfusion in a hypoxic region of a tissue in a subject. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description and non-limiting Examples.

BRIEF DESCRIPTION OF THE DRAWINGS

FIG. 1A depicts perfusion of the quadriceps muscle. At time 0, animals were infused i.v. with albumin (○, N=3), oxy-Hb (●, N=4), or SNO-Hb (■, N=7). FIG. 1B depicts tumor perfusion in rats infused i.v. with oxy-Hb (●, N=5, n=10) or albumin (○, N=3, n=3). FIG. 1C depicts tumor perfusion in rats infused i.v. with SNO-Hb (■, N=7, n=13), or SNO-albumin (□, N=7, n=14). "N" refers to the number of animals per group and "n" refers to the number of individual measurements. *$p<0.05$; **$p<0.01$ between t=0 and t=20 minutes (two-way ANOVA).

FIG. 3A is a graph depicting relative tumor perfusion in rats infused i.v. with SNO-Hb with the rats breathing room air (■, N=7, n=13) or 100% $O_2$ (□, N=7, n=13). FIG. 3B is a graph depicting relative tumor perfusion in rats infused i.v. with Oxy-Hb with the rats breathing room air (●, N=5, n=10) or 100% $O_2$ (○, N=4, n=8). Where indicated, $O_2$ breathing was administered from t=−5 minutes (arrowheads) to the end of the experiment; infusions were started at t=0. ***$p<0.005$ between t=0 and t=20 minutes (two-way ANOVA).

FIG. 4A depicts a time course of the vasoactive effects of SNO-Hb on tumor feeding arterioles determined from window chamber video analyses in rats breathing room air (■, N=4) or 100% $O_2$ (□, N=6). FIG. 4B depicts changes in muscle perfusion detected by Laser Doppler probes placed in the quadriceps muscle of tumor-bearing rats after SNO-Hb infusion. Rats breathed room air (■, N=7) or 100% $O_2$ (□, N=7). In FIG. 4B, *$p<0.05$ between t=0 and t=20 minutes (two-way ANOVA). FIG. 4C depicts changes in the mean arterial pressure (MAP) and FIG. 4D depicts changes in the heart rate (HR) following SNO-Hb infusion. Rats breathed room air (■, N=7) or 100% $O_2$ (□, N=7). FIG. 4E depicts changes in MAP and FIG. 4F depicts in HR following oxy-Hb infusion. Rats breathed room air (●, N=5) or 100% $O_2$ (○, N=5). In FIGS. 4C-4F, *$p<0.05$ at the indicated time points versus values at t=0 (Student's t test).

FIG. 5A depicts changes in perfusion simultaneously determined using Laser Doppler probes in rat tumors, and FIG. 5B depicts changes in perfusion simultaneously determined using Laser Doppler probes in the quadriceps muscle. In FIG. 5A, SNO-Hb was infused i.v. in animals breathing room air (■, N=7, n=13) or 100% $O_2$ (□, N=7, n=14), or i.a. with room air (▲, N=7, n=14) or 100% $O_2$ (Δ, N=7, n=13). Note the loss of $O_2$-dependence for i.a. infusions. In FIG. 5B, SNO-Hb was infused i.a. in animals breathing room air (▲, N=7) or 100% $O_2$ (Δ, N=6). FIG. 5C depicts changes in the mean arterial pressure (MAP) and FIG. 5D depicts changes in the heart rate (HR) following i.a. infusion of SNO-Hb. Rats breathed room air (▲, N=7) or 100% $O_2$ (Δ, N=7). In FIGS. 5C and 5D, *p<0.05 versus values at t=0 for the indicated time points (Student's t test).

FIGS. 6A-6D are plots depicting measurements of muscle or tumor perfusion in rats breathing 100% $O_2$ or 100% $O_2$ plus 100 parts per million ethyl nitrite (ENO). The first arrow indicates the start of the gas/gas mixture delivery, and the second arrow indicates the time at which the gas/gas mixture delivery is stopped. FIG. 6A is a graph depicting changes in $pO_2$ (mm Hg) in quadriceps muscle before, during, and after breathing 100% $O_2$ (□) or 100% $O_2$ plus 100 parts per million ENO (■). FIG. 6B is a graph depicting changes in $pO_2$ (mm Hg) in quadriceps muscle before, during, and after breathing room air plus 100 parts per million ENO (□). FIG. 6C is a graph depicting changes in $pO_2$ (mm Hg) in a tumor before, during, and after breathing 100% $O_2$ (□) or 100% $O_2$ plus 100 parts per million ENO (■). FIG. 6D is a graph depicting changes in $pO_2$ (mm Hg) in a tumor before, during, and after breathing room air plus 100 parts per million ENO (□). Note that in rats breathing 100 ppm ENO plus 100% $O_2$ the $pO_2$ increased from less than 10 mm Hg to greater than 10 mm Hg, but the same increase was not seen in tumors of rats breathing ENO under normoxic conditions.

DETAILED DESCRIPTION

Figure 1A:
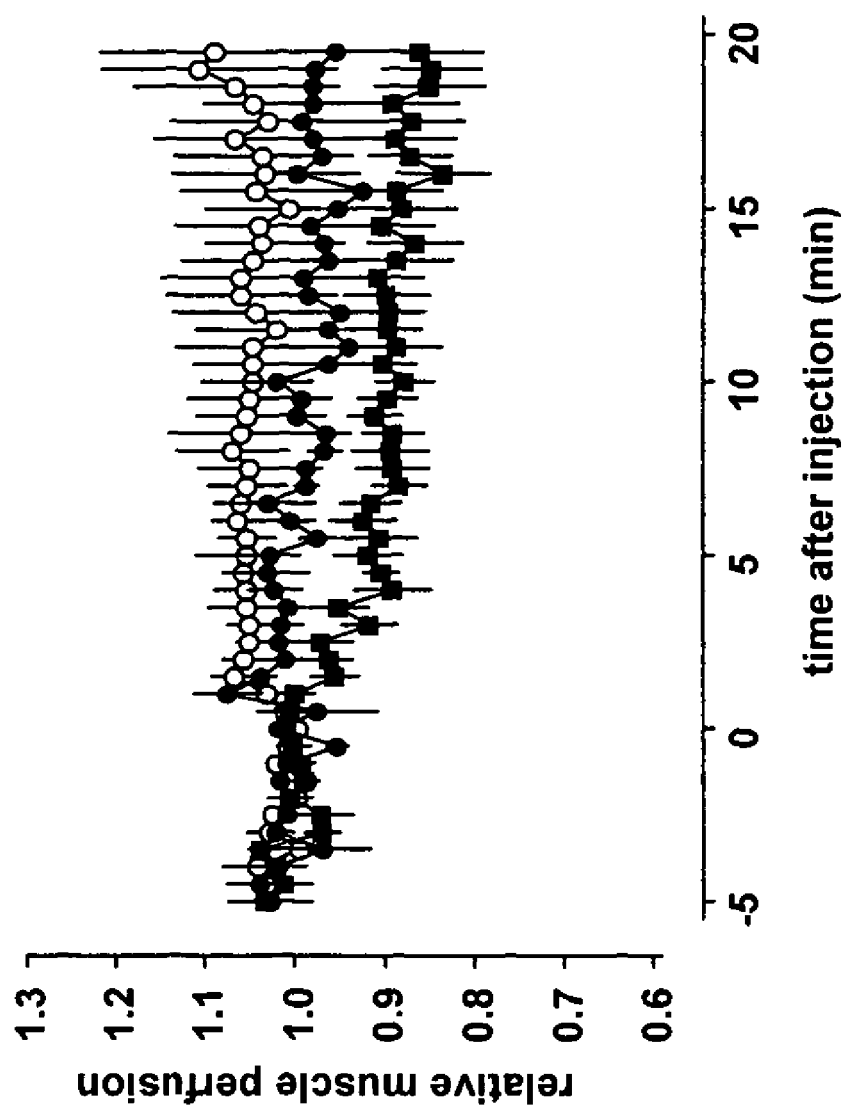
FIGS. 1A-1C depict time course plots of oxygenated hemoglobin (oxy-Hb)- and S-nitrosylated hemoglobin (SNO-Hb)-induced decreases in tumor blood flow. Changes in perfusion of muscle and tumors were determined by inserting Laser Doppler probes into the quadriceps muscle or tumors of rats breathing room air.

The most powerful sensitizer for radiotherapy is oxygen, and an agent with similar radiosensitizing properties is nitric oxide. As disclosed herein, a vasodilating agent is used to increase perfusion and maintain oxygenation of tumors during high oxygen content gas breathing. The vasodilating agent is capable of carrying NO to the tumor site and releases NO in a form that can increase radiosensitivity and/or chemosensitivity of the tumor at least in part by reducing tumor hypoxia and by providing NO in sufficient quantities to mimic oxygen in fixation of sublethal radiation or chemotherapy damage.

The steal effect arises as a consequence of the non tumor-selective vasoresponses to vasodilators. It prevents the clinical use of these agents for sensitizing tumors to radiation therapy and chemotherapy (Feron, 2004). Ethyl nitrite (ENO; also referred to as O-nitrosoethanol) has not been previously tested in this regard. ENO is a gas that can be delivered through airways to subjects and it does not reduce blood pressure. As such, it can react with fully-oxygenated hemoglobin (Hb) within red blood cells that transit through the lung vasculature, leading to the formation of S-nitrosylated Hb (SNO-Hb).

SNO-Hb is used to maintain perfusion and improve oxygenation of tumors during high oxygen content gas breathing. During hyperoxic gas breathing, nitrosohemoglobin releases NO in the distal arterioles, thereby opposing the vasoconstricting effects of hyperoxia. This effect improves delivery of oxygen and perfusion to tumor regions that might otherwise be hypoxic. Additionally, this vasodilating agent is capable of releasing NO in tumor regions in a form that can increase radiosensitivity and/or chemosensitivity of hypoxic regions by providing NO in sufficient quantities to mimic oxygen in fixation of sublethal radiation or chemotherapy damage, following exposure. Thus, the presently disclosed subject matter includes the combination of improved oxygen delivery and NO delivery to increase tumor radiosensitivity and/or chemosensitivity.

SNO-Hb is delivered to the tumor via red blood cells. The delivery occurs by having a tumor-bearing subject breathe a NO donor gas (such as ethyl nitrite) that is mixed with a hyperoxic gas, such as pure oxygen or carbogen (95% oxygen, 5% $CO_2$). The addition of hyperoxic gas breathing maintains Hb in the R-state, which prevents unloading of $O_2$ and SNO until the Hb enters into tumor regions, which are relatively hypoxic as compared to normal tissues. This approach maintains or improves perfusion and oxygen delivery to relatively hypoxic tumor regions.

I. DEFINITIONS

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a tumor cell" includes a plurality of such tumor cells, and so forth.

As used herein, the term "about," when referring to a value or to an amount of mass, weight, time, volume, concentration, or percentage is meant to encompass variations of in some embodiments, ±20%, in some embodiments ±10%, in some embodiments ±5%, in some embodiments 1%, and in some embodiments ±0.1% from the specified amount, as such variations are appropriate to perform the disclosed methods.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

As used herein, the term "subject" refers to any organism for which application of the presently disclosed subject matter would be desirable. The subject treated in the presently disclosed subject matter in its many embodiments is desirably a human subject, although it is to be understood that the principles of the presently disclosed subject matter indicate that the presently disclosed subject matter is effective with respect to all vertebrate species, including mammals, which are intended to be included in the term "subject". Moreover, a mammal is understood to include any mammalian species in which treatment of a tumor and/or a cancer is desirable, particularly agricultural and domestic mammalian species.

More particularly provided is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economic importance to humans. Thus, contemplated is the treatment of livestock, including, but not limited to, domesticated swine (pigs and hogs), ruminants, horses, poultry, and the like.

As used herein, the term "cell" is used in its usual biological sense. In some embodiments, the cell is present in an organism, for example, mammals such as humans, cows, sheep, apes, monkeys, swine, dogs, cats, and rodents. In some embodiments, the cell is a eukaryotic cell (e.g., a mammalian cell, such as a human cell). The cell can be of somatic or germ line origin, totipotent or pluripotent, dividing or non-dividing. The cell can also be derived from or can comprise a gamete or embryo, a stem cell, or a fully differentiated cell.

The term "tumor" as used herein encompasses both primary and metastasized solid tumors and carcinomas of any tissue in a subject, including, but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas. The term "tumor" also encompasses radioresistant and/or chemoresistant tumors, including, but not limited to radioresistant and/or chemoresistant variants of the any of the tumors listed above.

The terms "radiosensitivity" and "radiosensitive", as used herein to describe a tumor, refer to a quality of susceptibility to treatment using ionizing radiation. Thus, radiotherapy can be used to delay growth of a radiosensitive tumor. Radiosensitivity can be quantified by determining a minimal amount of ionizing radiation that can be used to delay tumor growth. Thus, the term "radiosensitivity" can refer to a quantitative range of radiation susceptibility.

The terms "sensitivity to chemotherapy", "chemosensitivity", and "chemosensitive", as used herein to describe a tumor, refer to a quality of susceptibility to treatment using chemotherapy. Thus, chemotherapy can be used to delay growth of a tumor sensitive to chemotherapy. Sensitivity of chemotherapy can be quantified by determining a minimal dosage of chemotherapy that can be used to delay tumor growth. Thus, the phrase "sensitivity to chemotherapy" can refer to a quantitative range of chemotherapy susceptibility.

The terms "radiation resistant tumor" and "radioresistant tumor" each generally refer to a tumor that is measurably less responsive to radiotherapy than are other tumors. Representative radiation resistant tumor models include glioblastoma multiforme and melanoma. Similarly, the terms "chemotherapy resistant tumor" and "chemoresistant tumor" generally refer to a tumor and/or to a tumor region that is measurably less responsive to chemotherapy than are other tumors and/or tumor regions.

The term "delaying tumor growth" refers to an increase in duration of time required for a tumor to grow a specified amount. For example, treatment with the compositions and/or methods disclosed herein can delay the time required for a tumor to increase in volume by a specified fraction (e.g., 2-fold, 3-fold, etc.) from an initial day of measurement (day 0), and/or can refer to an increase in the time required for the tumor to grow to a certain volume (e.g., 1 $cm^3$). Alternatively or in addition, the term "delayed" (and grammatical variants thereof) in the context of tumor growth can refer to a decrease in the rate at which a tumor grows and/or the rate at which individual cells of a tumor proliferate. As such, tumor growth delay in some embodiments can be considered relative to how the same tumor and/or tumor cell would have grown in the absence of treatment with the methods and/or compositions disclosed herein.

The term "increase," as used herein to refer to a change in radiosensitivity and/or sensitivity to chemotherapy of a tumor, refers to change that renders a tumor more susceptible to treatment by ionizing radiation and/or chemotherapy. Alternatively stated, an increase in radiosensitivity and/or chemosensitivity can refer to a decrease in the minimal amount of ionizing radiation and/or chemotherapy that effectively delays tumor growth. An increase in radiosensitivity and/or chemosensitivity can also comprise delayed tumor growth when a composition of the presently disclosed subject matter is administered with radiation and/or chemotherapy as compared to a same dose of radiation and/or chemotherapy alone. In some embodiments, an increase in radiosensitivity and/or chemosensitivity refers to an increase of at least about 2-fold, in some embodiments an increase of at least about 5-fold, and in some embodiments an increase of at least 10-fold. In some embodiments of the presently disclosed subject matter, an increase in radiosensitivity and/or chemosensitivity comprises a transformation of a radioresistant and/or chemoresistant tumor to a radiosensitive and/or chemosensitive tumor.

The term "tumor regression" generally refers to any one of a number of indices that suggest change within the tumor to a less developed form. Such indices include, but are not limited to a destruction of tumor vasculature (for example, a decrease in vascular length density or a decrease in blood flow), a decrease in tumor cell survival, a decrease in tumor volume, and/or a decrease in tumor growth rate. Methods for assessing tumor growth delay and tumor regression are known to one of ordinary skill in the art.

II. COMPOSITIONS

The presently disclosed subject matter provides in some embodiments compositions comprising one or more of a nitrosylated hemoglobin, an agent that induces nitrosylation of hemoglobin in the subject, a hemoglobin and an agent that induces nitrosylation of hemoglobin in the subject, and combinations thereof. As such, the compositions disclosed herein are designed in some embodiments to deliver to, or produce in, a subject a nitrosylated hemoglobin.

Thus, in some embodiments the compositions disclosed herein comprise a hemoglobin that has been nitrosylated prior to administration to a subject. Any nitrosylation methods can be used to nitrosylate the hemoglobin to be administered, and include, but are not limited to the methods disclosed in the Materials and Methods used in EXAMPLES 1-5 presented hereinbelow. Thus, a hemoglobin or hemoglobin substitute can be modified in vitro or in vivo prior to administration to a subject. In some embodiments, the hemoglobin is present within a red blood cell.

Additionally, in some embodiments the compositions disclosed herein comprise an agent that induces nitrosylation of hemoglobin in the subject. As used herein, the phrase "an agent that induces nitrosylation of hemoglobin in a subject" refers to any agent that when administered to a subject results in a higher level of hemoglobin nitrosylation in the subject than would have been present in the subject in the absence of the agent. A representative agent that induces nitrosylation of hemoglobin in a subject comprises a nitric oxide donor.

In some embodiments, a nitric oxide donor comprises ethyl nitrite (ENO). It is understood, however, that other NO donors can be employed in the practice of the presently disclosed subject matter, with the proviso that the NO donor is capable of nitrosylating hemoglobin in vitro and/or in vivo, optionally endogenous hemoglobin present within a red blood cell. Other NO donors include, but are not limited to S-nitrosoglutathione (GSNO) and ethyl nitrate ($ENO_2$).

Additionally, the route of administration of the agent (e.g., a NO donor) is not to be viewed as a limitation of the presently disclosed subject matter. Therefore, while in some embodiments an NO donor is provided in a breathable gas, NO donors can also be administered for example in an oral form, in the form of intravenous, intra-arterial, intramuscular, subcutaneous, or other injectable form, provided that the administration of the NO donor results in an increased level of nitrosylation of hemoglobin in the subject (e.g., the subject's own hemoglobin and/or an administered hemoglobin or hemoglobin product).

In some embodiments, the agent that induces nitrosylation of hemoglobin in the subject is capable of nitrosylating hemoglobin present within a red blood cell that is already in the subject. The red blood cell can be one of the subject's own red blood cells or can be a red blood cell that was administered to the subject.

In some embodiments, the compositions further comprise a hyperoxic gas. As used herein, the phrase "hyperoxic gas" refers to a gas that comprises an oxygen content that is greater than that found in normal room air (i.e., about 21%). Thus, a "hyperoxic gas" is a gas that includes, for example, about 100%, 95%, 90%, 85%, 80%, 75%, 70%, 65%, 60%, 55%, 50%, 45%, 40%, 35%, 30%, or 25% oxygen. In some embodiments, a hyperoxic gas is 100% oxygen, and in some embodiments a hyperoxic gas is carbogen (about 95% oxygen, about 5% carbon dioxide).

Breathing hyperoxic gas can lead to vasoconstriction, which can negatively impact the ability of the hyperoxic gas to deliver increased oxygen to a target tissue (e.g., a region of hypoxia). Accordingly, the hyperoxic gas is mixed in some embodiments with a vasodilation agent such as nitric oxide and/or a nitric oxide donor including, but not limited to an alkyl nitrite such as C1-C6 straight chain, branched, or substituted alkyl nitrite (e.g., ethyl nitrite). While applicants do not wish to be bound by any particular theory of operation, a nitric oxide donor is chosen that is capable of nitrosylating hemoglobin either in vitro or in vivo, including hemoglobin that is within a red blood cell or not within a red blood cell.

III. METHODS OF TREATMENT

III.A. Methods for Increasing Perfusion

The presently disclosed subject matter provides in some embodiments methods for treating conditions associated with hypoxia. As used herein, the phrase "condition associated with hypoxia" refers to any disease and/or disorder, and/or any symptom thereof, which results from and/or is exacerbated or aggravated by hypoxia. Exemplary conditions associated with hypoxia include, but are not limited to tumors, cancers, peripheral vascular diseases, diabetes, diseases related to smoking, cirrhosis, rheumatoid arthritis, stroke, myocardial infarction, and combinations thereof. Accordingly, the methods and compositions disclosed herein can be employed to treat and/or ameliorate at least one symptom of these conditions.

As disclosed herein, certain diseases and/or disorders associated with hypoxia, and/or one or more symptoms thereof, can be treated by reducing hypoxic regions of relevant tissues in a subject. This can be accomplished in any manner including, but not limited to delivering more oxygen to the tissue such as by increasing perfusion in a hypoxic region of the tissue.

Accordingly, the presently disclosed subject matter provides in some embodiments methods for increasing perfusion in a hypoxic region of a tissue in a subject. In some embodiments, the methods comprise administering to the subject an inhalable composition comprising ethyl nitrite (ENO) and optionally a hyperoxic gas.

Increasing perfusion can also lead to other beneficial outcomes. For example, it is also expected that the distribution of other agents delivered by the blood to a tumor would be enhanced using the methods and compositions disclosed herein. Exemplary, non-limiting agents include diagnostic, therapeutic, and/or prognostic agents such as contrast agents using for functional imaging of tumors.

III.B. Methods for Treating Tumors and/or Cancers

The presently disclosed subject matter also provides methods for treating subjects with particular conditions associated with hypoxia. In some embodiments, a condition associated with hypoxia is a tumor and/or a cancer. In some embodiments, the methods and compositions disclosed herein are part of a combination therapy as discussed in more detail hereinbelow.

In some embodiments, the presently disclosed subject matter relates to methods for delaying tumor growth in a subject. In some embodiments, the methods comprise administering to the subject a composition selected from the group consisting of a nitrosylated hemoglobin, an agent that induces nitrosylation of hemoglobin in the subject, a hemoglobin and an agent that induces nitrosylation of hemoglobin in the subject, and combinations thereof, optionally in combination with a hyperoxic gas. In some embodiments, the administering increases $pO_2$ in a plurality of cells of the tumor to above about 10 mm Hg, whereby tumor growth in the subject is delayed. In some embodiments, the hyperoxic gas is selected from the group consisting of pure oxygen and carbogen. In some embodiments, the administering step increases $pO_2$ in a plurality of cells of the tumor to above about 10 mm Hg. In some embodiments, $pO_2$ is monitored in the tumor in real time to ensure that it is at least about 10 mm Hg. In some embodiments, the methods also comprise treating the tumor with radiation therapy, chemotherapy, or both radiation therapy and chemotherapy.

Additionally, the presently disclosed subject matter relates in some embodiments to methods for inhibiting tumor blood vessel growth in a subject. In some embodiments, the methods comprise administering to the subject an inhalable composition comprising ethyl nitrite (ENO) and optionally a hyperoxic gas (for example, a hyperoxic gas selected from the group consisting of pure oxygen and carbogen). In some embodiments, the administering step increases $pO_2$ in a plurality of cells of the tumor to above about 10 mm Hg. In some embodiments, the methods further comprise and (b) treating the tumor with radiation therapy, chemotherapy, or both radiation therapy and chemotherapy. As used herein, such an inhibition need not be absolute, but can include a decrease in a rate and/or extent of tumor angiogenesis that results from employing the methods and/or compositions disclosed herein.

IV. METHODS FOR ENHANCING DELIVERY OF DIAGNOSTIC, THERAPEUTIC, AND/OR PROGNOSTIC AGENTS

The presently disclosed subject matter also provides methods for enhancing delivery of a diagnostic, therapeutic, or prognostic agent to a target tissue including, but not limited to a tumor, in a subject. In some embodiments, the methods comprise (a) administering to the subject a composition selected from the group consisting of a nitrosylated hemoglobin, a nitrosylation agent that induces nitrosylation of hemoglobin in the subject, a hemoglobin and a nitrosylation agent that induces nitrosylation of hemoglobin in the subject, and combinations thereof; and (b) administering the diagnostic, therapeutic, or prognostic agent to the subject, wherein delivery of the diagnostic, therapeutic, or prognostic agent to a tumor in the subject is enhanced. The compositions and methods disclosed herein can be employed to increase perfusion and/or blood flow in target tissues including, but not limited to hypoxic regions of tumors. In some embodiments, the methods further comprise administering to the subject a hyperoxic gas selected from the group consisting of 100% oxygen and carbogen.

Accordingly, the compositions and methods disclosed herein can be employed to enhance delivery of diagnostic, therapeutic, and prognostic agents that are carried via the bloodstream (e.g., agents that are injected intravenously) by enhancing blood flow in the target tissue. The delivery of any such agent can be enhanced, including but not limited to therapeutic agents such as drugs and diagnostic and/or prognostic agents such as imaging agents. Particularly with respect to imaging agents that cannot be conveniently administered directly to a target tissue, the ability to increase the delivery of the imaging agent by employing the compositions and methods disclosed herein can result in greater capacity to image the target tissue, less time the subject must spend in the imaging apparatus, a lower dose of imaging agent that is required for acceptable imaging, and combinations thereof. Particularly with respect to imaging agents that have known toxicity associated with their use, the ability to use less of the agent can be a considerable advantage.

V. COMBINATION THERAPIES

Tumors and/or cancers can be treated using combination therapies comprising combinations of surgery, radiotherapy, and/or chemotherapy, and/or other therapies include, but not limited to photodynamic therapy (PDT) and immunotherapy (IT). Thus, the presently disclosed subject matter can be employed as a part of a combination therapy. As used herein, the phrase "combination therapy" refers to any treatment wherein the methods and compositions disclosed herein are used in combination with another therapy including, but not limited to radiation therapy (radiotherapy), chemotherapy, surgical therapy (e.g., resection), PDT, IT, and combinations thereof.

As disclosed herein, various therapies that are employed to treat neoplastic disease can be relatively ineffective if the tumor and/or cancer includes localized regions of hypoxia. This is based at least in part on the requirement for the therapy to generate free radicals from oxygen, which does not occur in hypoxic sites.

As a result, the methods and/or compositions disclosed herein can be employed to enhance the effectiveness of a second treatment such as radiotherapy, chemotherapy, photodynamic therapy, immunotherapy, and combinations thereof. In these embodiments, the methods relate to increasing the sensitivity of a tumor and/or a tumor cell in a subject to a treatment, and in some embodiments the methods comprise administering to the subject an inhalable composition comprising ethyl nitrite (ENO) and optionally a hyperoxic gas, which further optionally can be selected from the group consisting of pure oxygen and carbogen, whereby $pO_2$ in a plurality of cells of the tumor is increased to above about 10 mm Hg, thereby increasing sensitivity of the tumor to the second treatment (e.g., a treatment selected from the group consisting of radiotherapy, chemotherapy, photodynamic therapy, immunotherapy, and combinations thereof.

V.A Radiation Treatment

In some embodiments, the methods and compositions disclosed herein are employed in a combination therapy with radiation treatment. For such treatment of a tumor, the tumor is irradiated concurrent with, or subsequent to, administration of an inhalable composition as disclosed herein. One of skill in the medical art can design, upon consideration of the instant disclosure, an appropriate dosing schedule for treating a subject with radiation in conjunction with the compositions and methods disclosed herein. For example, tumors can be irradiated with brachytherapy utilizing high dose rate or low dose rate brachytherapy internal emitters.

In order to enhance the benefit gained from administration of the compositions disclosed herein, the timing of administration of the composition and the radiation treatment should be adjusted such that the $pO_2$ in the tumor to be treated is at least about 10 mm Hg during at least a portion of the entire period when the radiation is being administered (optionally, during the entire period). Accordingly, the composition can be administered beginning, for example, 5, 10, 15, 20, 30, 45, or 60 minutes before the radiation treatment is administered. Additionally, the subject can continue to breathe the composition while the radiation treatment is being administered. Upon cessation of the radiation treatment, the administration of the composition can also be terminated.

It is understood that since radiotherapy typically is repeated several times in order to affect a maximal response, the administration of the composition can likewise be repeated each time radiotherapy is given. Thus, the time course over which a inhalable composition as disclosed herein is administered can comprise in some embodiments a period of several weeks to several months coincident with radiotherapy, but in some embodiments can extend to a period of 1 year to 3 years as needed to effect tumor control. Alternatively, a composition can be administered prior to an initial radiation treatment and then at desired intervals during the course of radiation treatment (e.g., weekly, monthly, or as required).

Subtherapeutic or therapeutic doses of radiation can be used for treatment of a tumor and/or a cancer as disclosed herein. In some embodiments, a subtherapeutic or minimally therapeutic dose (when administered alone) of ionizing radiation is used. For example, the dose of radiation can comprise in some embodiments at least about 2 Gy ionizing radiation, in some embodiments about 2 Gy to about 6 Gy ionizing radiation, and in some embodiments about 2 Gy to about 3 Gy ionizing radiation. When radiosurgery is used, representative doses of radiation include about 10 Gy to about 20 Gy administered as a single dose during radiosurgery or about 7 Gy administered daily for 3 days (about 21 Gy total). When high dose rate brachytherapy is used, a representative radiation dose comprises about 7 Gy daily for 3 days (about 21 Gy total). For low dose rate brachytherapy, radiation doses typically comprise about 12 Gy administered twice over the course of 1 month. $^{125}$I seeds can be implanted into a tumor can be used to deliver very high doses of about 110 Gy to about 140 Gy in a single administration.

Radiation can be localized to a tumor using conformal irradiation, brachytherapy, stereotactic irradiation, intensity modulated radiation therapy (IMRT), and/or can be localized to a tumor by employing vectors that comprise, but are not limited to, proteins, antibodies, liposomes, lipids, nanoparticles, and combinations thereof. The threshold dose for treatment can thereby be exceeded in the target tissue but avoided in surrounding normal tissues. For treatment of a subject having two or more tumors, local irradiation enables differential drug administration and/or radiotherapy at each of the two or more tumors. Alternatively, whole body irradiation can be used, as permitted by the low doses of radiation required following radiosensitization of the tumor.

Radiation can also comprise administration of internal emitters, for example $^{131}$I for treatment of thyroid cancer, NETASTRON™ and QUADRAGEN® pharmaceutical compositions (Cytogen Corp., Princeton, N.J., United States of America) for treatment of bone metastases, $^{32}$P for treatment of ovarian cancer. Other internal emitters include $^{125}$I, iridium, and cesium. Internal emitters can be encapsulated for administration or can be loaded into a brachytherapy device.

Radiotherapy methods suitable for use in the practice of presently disclosed subject matter can be found in Leibel & Phillips, 1998, among other sources.

V.B. Chemotherapy Treatment

In some embodiments, the methods and compositions disclosed herein are employed in a combination therapy with chemotherapy. Particular chemotherapeutic agents are generally chosen based upon the type of tumor to be treated, and such selection is within the skill of the medical professional.

Chemotherapeutic agents are generally grouped into several categories including, but not limited to DNA-interactive agents, anti-metabolites, tubulin-interactive agents, hormonal agents, and others such as asparaginase or hydroxyurea. Each of the groups of chemotherapeutic agents can be further divided by type of activity or compound. For a detailed discussion of various chemotherapeutic agents and their methods for administration, see Dorr et al., 1994, herein incorporated by reference in its entirety.

In order to reduce the mass of the tumor and/or stop the growth of the cancer cells, a chemotherapeutic agent should prevent the cells from replicating and/or should interfere with the cell's ability to maintain itself. Exemplary agents that accomplish this are primarily the DNA-interactive agents such as Cisplatin, and tubulin interactive agents.

DNA-interactive agents include, for example, alkylating agents (e.g., Cisplatin, Cyclophosphamide, Altretamine); DNA strand-breakage agents (e.g., Bleomycin); intercalating topoisomerase II inhibitors (e.g., Dactinomycin and Doxorubicin); non-intercalating topoisomerase II inhibitors (e.g., Etoposide and Teniposide); and the DNA minor groove binder Plicamycin.

Generally, alkylating agents form covalent chemical adducts with cellular DNA, RNA, and/or protein molecules, and with smaller amino acids, glutathione, and/or similar biomolecules. These alkylating agents typically react with a nucleophilic atom in a cellular constituent, such as an amino, carboxyl, phosphate, or sulfhydryl group in nucleic acids, proteins, amino acids, or glutathione.

Anti-metabolites interfere with the production of nucleic acids by either of two major mechanisms. Some of the drugs inhibit production of deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts.

Hydroxyurea appears to act primarily through inhibition of the enzyme ribonucleotide reductase.

Asparaginase is an enzyme which converts asparagine to nonfunctional aspartic acid and thus blocks protein synthesis in the tumor.

Tubulin interactive agents act by binding to specific sites on tubulin, a protein that polymerizes to form cellular microtubules. Microtubules are critical cell structure units. When the interactive agents bind on the protein, the cell can not form microtubules. Tubulin interactive agents include Vincristine and Vinblastine, both alkaloids and Paclitaxel.

Adrenal corticosteroids are derived from natural adrenal cortisol or hydrocortisone. They are used because of their anti-inflammatory benefits as well as the ability of some to inhibit mitotic divisions and to halt DNA synthesis. These compounds include Prednisone, Dexamethasone, Methylprednisolone, and Prednisolone.

The hormonal agents and leutinizing hormones are not usually used to substantially reduce the tumor mass. However, they can be used in conjunction with the chemotherapeutic agents. Hormonal blocking agents are also useful in the treatment of cancers and tumors. They are used in hormonally susceptible tumors and are usually derived from natural sources. These include, but are not limited to estrogens and conjugated estrogens, progestins, and androgens. Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes. Other anti-hormonal agents include anti-estrogenic agents, anti-androgen agents, and anti-adrenal agents such as Mitotane and Aminoglutethimide.

VI. OTHER OXYGEN-DEPENDENT TREATMENTS

Various other oxygen-dependent therapies can be employed that would be expected to benefit from the presently disclosed compositions and methods. Examples of therapies that could benefit from a combined treatment regimen employing the methods and/or compositions disclosed herein include any antitumor therapies wherein an active agent reaches the tumor from the systemic circulation. Such therapies include, but are not limited to, photodynamic therapy, hormone therapy, immunotherapy, gene therapy, antivascular therapy, antiangiogenic therapy, cell therapy (based on injection or mobilization of cells with an antitumor activity), and combinations thereof, including any of these therapies further in combination with radiotherapy and/or chemotherapy. Circulating antitumor agents for which therapeutic efficacy can be increased through administration of the compounds disclosed herein include ions, small molecules, macromolecules, peptides, proteins, nucleotides, virus, liposomes, emulsions, bacteria, immune cells, stem cells, and combination (s) thereof.

One further therapy that can benefit from the methods and compositions disclosed herein is photodynamic therapy (PDT). The therapeutic effect of PDT is highly dependent upon oxygen availability. PDT involves two individual inactive components that are combined to induce cellular and tissue effects in an $O_2$-dependent manner (Dolmans et al., 2003). The first component is the photosensitizer (e.g., porphirins), which localizes to the tumor. The second component involves the administration of light of a specific wavelength that activates the photosensitizer. In situ, the activated photosensitizer transfers energy from light to $O_2$ to generate reactive oxygen species, which then mediate cellular toxicity. The biological responses are activated only in the particular areas of tissue that have been exposed to light and contain sufficient amounts of $O_2$. The toxic species formed with PDT is singlet oxygen. Thus, the cytotoxic effects of PDT drugs are entirely $O_2$-dependent and photosensitization typically does not occur in hypoxic tumor areas. As a result, increasing the local concentration of oxygen in a tissue targeted for PDT (e.g., a hypoxic region of a tumor) can be expected to enhance the efficacy of the PDT in that target tissue.

Another approach to tumor and/or cancer treatment is immunotherapy. Immunotherapy generally relates to strategies designed to augment the ability of the subject's immune system to recognize tumor cells and eliminate them. Typically, these strategies are intended to boost and/or to activate antitumor lympocytes. A non-limiting example of immunotherapy relates to the use of therapeutic vaccines. Naked peptides, peptides loaded on protein carriers, and/or antigen presenting cells loaded with peptide can also elicit an antitumor response in vivo in subjects. Responses generally involve the activation of antitumor T lymphocytes, but also can include activation of other immunomodulatory cells including, but not limited to memory lymphocytes, natural killer cells, and B lymphocytes.

Heterologous or autologous immune transfer can also be a part of an antitumor treatment strategy, and all these approaches are expected to benefit from the presently disclosed subject matter because immune cells enter the tumor through the systemic circulation and need oxygen to live, to multiply, and to act in a hypoxic environment. See e.g., U.S. Pat. No. 5,405,940 and progeny thereof (including, but not limited to U.S. Pat. Nos. 5,462,871; 5,695,994; 6,034,214; 6,222,012; 6,379,901; and 6,488,932); PCT International Patent Application Publications WO 94/05304; WO 94/16713; WO 95/25530; WO 95/33855; WO 96/29409; WO 98/32855; and WO 98/58956; van Baren et al. 2005; Godelaine et al., 2003; Chaux et al., 1999; Van den Eynde et al., 1995; van der Bruggen et al., 1994; Gaugler et al., 1994; Boon et al., 1994; Traversari et al., 1992; and other patents, published patent applications, and scientific publications from Dr. Thierry Boon and co-workers (each of which is incorporated by reference herein in its entirety) for discussion of MAGE and MAGE-related approaches to antitumor therapy, several of which are currently in clinical trials.

Other immunotherapeutic strategies are designed to affect the anti-tumor activities of the subject's macrophages, which are frequently found in close association with tumors (e.g., so-called "tumor-associated macrophages (TAMs); see Lewis & Murdoch, 2005 for a review). In some cases, macrophages can comprise up to 80% of the cell mass in certain tumors (see Bingle et al., 2002).

Macrophage recruitment to tumors results in alterations in the tumor microenvironment, and is a strongly negative predictive factor for outcome. For example, it has been shown that hypoxic areas of tumors attract macrophages and macrophage precursors (Murdoch et al., 2004), and that the macrophage response to hypoxia can actually increase the ability of the tumor cells to proliferate and/or metastasize (see Lewis & Murdoch, 2005, and references therein). Macrophage responses to hypoxia include the production of various growth factors relevant to tumor cell proliferation and angiogenesis (e.g., epidermal growth factor, vascular endothelial growth factor) as well as the production of immunomodulatory factors such as prostaglandin $E_2$ and IL-10 that can downregulate the anti-tumor response of various immune effector cells.

Additionally, hypoxia inhibits the phagocytosis of tumor cells and other necrotic cells by macrophages. Taken together, therefore, it is clear that hypoxia alters macrophage biological activities in ways that alone or in combination can severely negatively impact the ability of the subject's immune system to respond to the presence of tumor and/or cancer cells.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods Used in Examples 1-6

Rats and Tumors. Female Fischer 344 rats (Charles River Laboratories, Raleigh, N.C., United States of America), bearing or not bearing the syngeneic mammary adenocarcinoma R3230AC (Hilf et al., 1965), were used in all experiments. Tumor pieces from donor rats were implanted in anesthetized animals (100 mg/Kg ketamine and 10 mg/Kg xylazine i.p.). Tumors were grown in the subcutis of the left lateral quadriceps muscle or, for window chamber experiments, between two fascial layers on the back of rats. Animals were then randomly assigned to treatment groups. Further interventions/observations were performed on anesthetized animals (50 mg/Kg pentobarbital i.p.) maintained at 37° C. on a temperature-controlled thermal blanket. Where indicated, some rats were fitted with a facemask for breathing 100% $O_2$. All experiments were approved by the Duke University Institutional Animal Care and Use Committee.

Drugs. SNO-Hb was synthesized through reaction of purified human hemoglobin $A_0$ (Apex Bioscience, Durham, N.C., United States of America) with SNO-cysteine in non-acidic conditions as described in McMahon & Stamler, 1999. Solutions of purified human hemoglobin $A_0$ (Apex Bioscience, Durham, N.C., United States of America) were dialyzed overnight at 4° C. against 2% (w/v) aerated sodium tetraborate pH 9.2, 0.5 mmol/L EDTA. For SNO-Hb synthesis, L-cysteine hydrochloride (0.55 mol/L in 0.5 mol/L HCl, 0.5 mol/L EDTA) was first reacted with an equal volume of 0.5 mol/L $NaNO_2$ to yield Cys-NO. Then, a 10-fold molar excess of Cys-NO was reacted with dialyzed oxy-Hb at a 1:20 (v/v) ratio for 10 minutes. The reaction was terminated by centrifugation through a fine Sephadex G-25 chromatography column (Pharmacia Biotech, Uppsala, Sweden) equilibrated with PBS, pH 7.4, 0.5 mmol/L EDTA. Under these conditions, the yield of oxy-Hb S-nitrosylation was consistently 1.9 S-nitroso-cysβ93 per tetramer.

SNO-albumin was synthesized by reacting an equal volume of bovine serum albumin (0.2 mmol/L in HCl 0.1 mmol/L, 0.5 mmol/L EDTA) with 0.2 mmol/L $NaNO_2$ for 30 minutes. All solutions (diluted at 200 µmol/L in PBS pH 7.4, 0.5 mmol/L EDTA) were kept on ice or frozen and protected from light until administration. Less than 2-weeks old solutions were infused at a dose of 200 nmol/Kg in 0.25 ml, immediately followed by a 0.25 ml delivery of saline. Assuming a plasma volume of about 3 ml per 100 g in rats and no significant partition in blood cells, this dose would achieve a maximum plasma concentration of about 6.5 µmol/L for all drugs. To avoid volume-induced alterations of hemodynamics, solutions were infused at 0.5 ml/minutes from time 0.

Surgery. For i.v. infusions, the femoral artery and vein were cannulated and drugs were infused through the venous cannula. For i.a. infusions, the femoral and left carotid arteries were cannulated and drugs were infused through the carotid cannula. For window chamber experiments, the two window frames were surgically positioned in the dorsal skin flap, followed by tumor cell transplantation to the chamber tissue, as described in Dewhirst et al., 1996. Following several days of tumor growth, direct visualization of tumor-feeding arterioles was performed using intravital microscopy.

Blood Gas and Hemoglobin Saturation Measurements in Tumor Microvessels. Blood gases and Hb oxygen saturation were measured using a 1640 oximeter coupled to a 482 co-oximeter (Instrumentation Laboratories, Lexington, Mass., United States of America) from 0.5 ml samples of femoral arterial and venous blood. For tumor microvessels in window chambers, Hb saturation was calculated from transmission optical measurements of vascular absorbance using a hyperspectral imaging technique described in Sorg et al., 2005. A liquid crystal tunable filter (CRI, Inc., Woburn, Mass., United States of America) placed in front of a CCD camera (DVC Company, Austin, Tex., United States of America) was used for band-limited imaging.

Blood Flow. Blood flow was measured using Laser Doppler flowmetry. For flank tumor experiments, 300 µm diameter Laser Doppler probes (OxiFlo, Oxford Optronix, Oxford, United Kingdom) were simultaneously inserted into the tumor and quadriceps muscle of each animal. For window chamber experiments, Laser Doppler probes (LASERFLO®, TSI, St. Paul, Minn., United States of America) were positioned beneath the tumor window as described in Dunn et al., 1999.

SNO-Hb Assay. The determination of SNO-Hb concentrations was based on a reaction where cleavage of S-nitrosothiols yields a nitrosant that activates 4,5-diaminofluorescein (DAF-2, Sigma, St. Louis, Mo., United States of America). Briefly, blood samples were collected in heparinized tubes just before infusion and at 1 minute, 5 minutes, and every 5 minutes after infusion of SNO-Hb i.v. for 30 minutes. Plasma (100 µl) was immediately mixed with DAF-2 (30 µM final concentration). Half of this solution was then reacted for 10 minutes with an equal volume of 1.2 mM $HgCl_2$. The reaction was terminated by centrifugation in filter tubes (Nanosep, Pall, East Hills, N.Y., United States of America). Upon light excitation at 485 nm, DAF-2-associated light emission was read at 520 nm. SNOs were quantified as the difference in fluorescence signals generated in the presence and absence of $HgCl_2$, which specifically cleaves SNOs, yielding nitrite. Data acquired before drug infusion allowed basal SNO levels to be determined. The plasma half-life of SNO-Hb was calculated from exponential decay curves fitting each experimental curve. Hb concentration in plasma samples was determined by visible spectrophotometry.

Vascular Reactivity In Vivo. Tumor-feeding arterioles in window chambers were visualized using transillumination. Arteriolar diameters were measured from videotaped images using an image-shearing monitor (IPM Inc., San Diego, Calif., United States of America).

Mean Arterial Pressure and Heart Rate. Mean arterial pressure (MAP) and heart rate (HR) were measured with a blood pressure analyzer (Digi-Med, Micro-Med, Louisville, Ky., United States of America) connected to the femoral artery cannula as described in Dewhirst et al., 1996.

Statistical Analyses. All values are shown in the Figures as means ±S.E. Time curves were normalized to the baseline before infusion. "N" refers to the number of animals per group, and "n" to individual measurements. Repeated-measure two-way ANOVA or Student's t tests were used as indicated.

Example 1

SNO-Hb and Oxy-Hb i.v. Reduce Muscle and Tumor Perfusion in Normoxic Rats

Whether i.v. infusion of human cell-free oxy-Hb and SNO-oxy-Hb (SNO-Hb) influenced muscle perfusion in the quadriceps of rats breathing room air (normoxia) was investigated. SNO-Hb decreased muscle perfusion more than Hb when compared to albumin (see FIG. 1A, p=0.055 and 0.3 vs. albumin, respectively; two-way ANOVA).

Figures 1B, 1C:
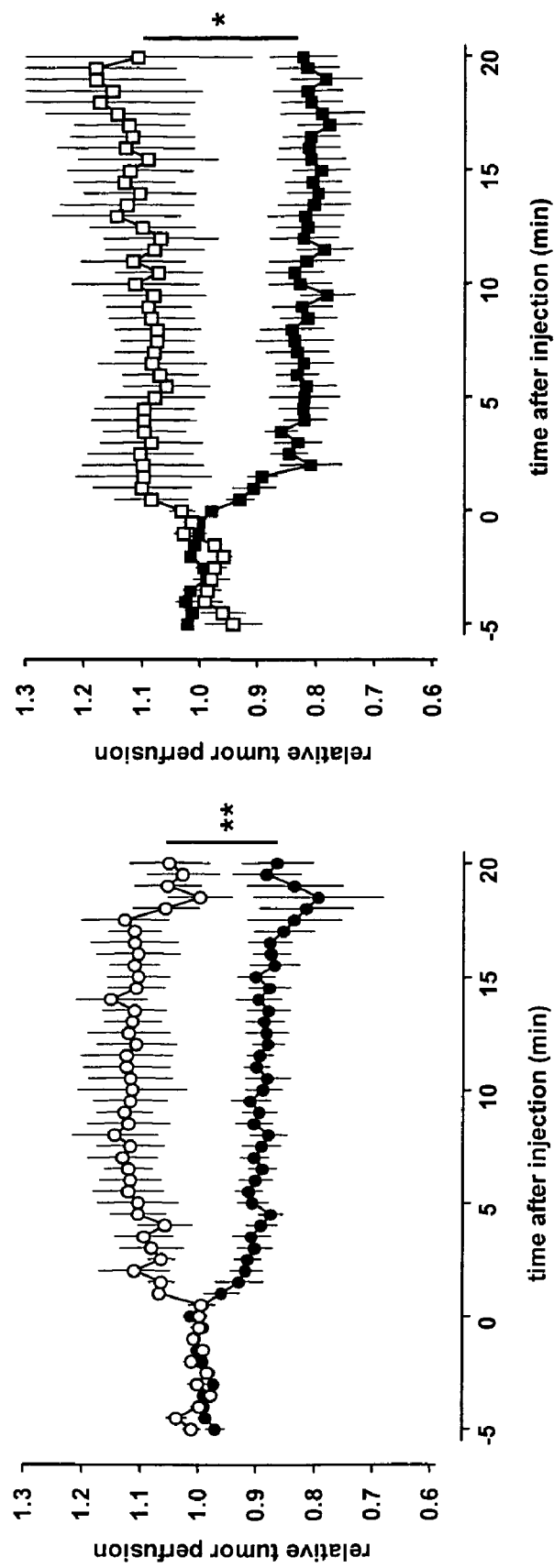

The pharmacological effects of these molecules in flank tumors of normoxic rats was then determined. In contrast to albumin, Hb induced a rapid and sustained decrease in tumor blood flow (see FIG. 1B, p<0.01 vs. albumin; two-way ANOVA). Unexpectedly, i.v. infusion of SNO-Hb also reduced perfusion (see FIG. 1C, p<0.05 vs. SNO-albumin; two-way ANOVA). Reductions in flow caused by oxy-Hb and SNO-Hb were not different (p>0.05; two-way ANOVA). However, the effects of the two Hbs were quite different from the small increase in tumor perfusion that was observed following albumin or SNO-albumin infusion i.v. (see FIGS. 1B and 1C). The effects of SNO-albumin and albumin were not significantly different (p>0.05; two-way ANOVA).

Example 2

Hyperoxia Prolongs the Half-life and Modulates the Pressor Activity of Cell-Free SNO-Hb It was reasoned that an increase in plasma oxygenation might stabilize SNO-Hb, increase peripheral delivery, and thereby increase the bioactivity in tumors. Thus, whether the plasma half-life of SNO-Hb i.v. was prolonged in rats breathing 100% $O_2$ (hyperoxia) versus room air was determined. Blood gas measurements showed that breathing 100% $O_2$ induced significant increases in venous and arteriolar blood $pO_2$, $pCO_2$, and endogenous Hb oxygen saturation ($HbO_2$). Changes in Hb saturation were identical in femoral vein and tumor venules. Changes were less pronounced in tumor-feeding arterioles versus the femoral artery, as expected from blood deoxygenation along the arterial tree and at the tumor margin (see Table 1).

TABLE 1

Blood Gas and Hemoglobin Saturation Measurements.

|  | Room Air | 100% $O_2$ |
|---|---|---|
| Femoral artery: | | |
| $pO_2$ (mm Hg) | 82.4 ± 0.4 | 435.5 ± 34.7* |
| $pCO_2$ (mm Hg) | 49.6 ± 1.3 | 56.9 ± 1.7* |
| $HbO_2$ (%) | 88.8 ± 0.4 | 98.2 ± 0.1* |
| Femoral vein | | |
| $pO_2$ (mm Hg) | 57.5 ± 1.2 | 69.8 ± 3.0* |
| $pCO_2$ (mm Hg) | 50.6 ± 1.7 | 72.0 ± 2.1* |
| $HbO_2$ (%) | 67.7 ± 2.4 | 75.8 ± 3.4* |
| Tumor artery | | |
| $HbO_2$ (%) | 76 ± 2 | 89 ± 2* |
| Tumor vein | | |
| $HbO_2$ (%) | 69 ± 2 | 78 ± 3* |

Figure 2:
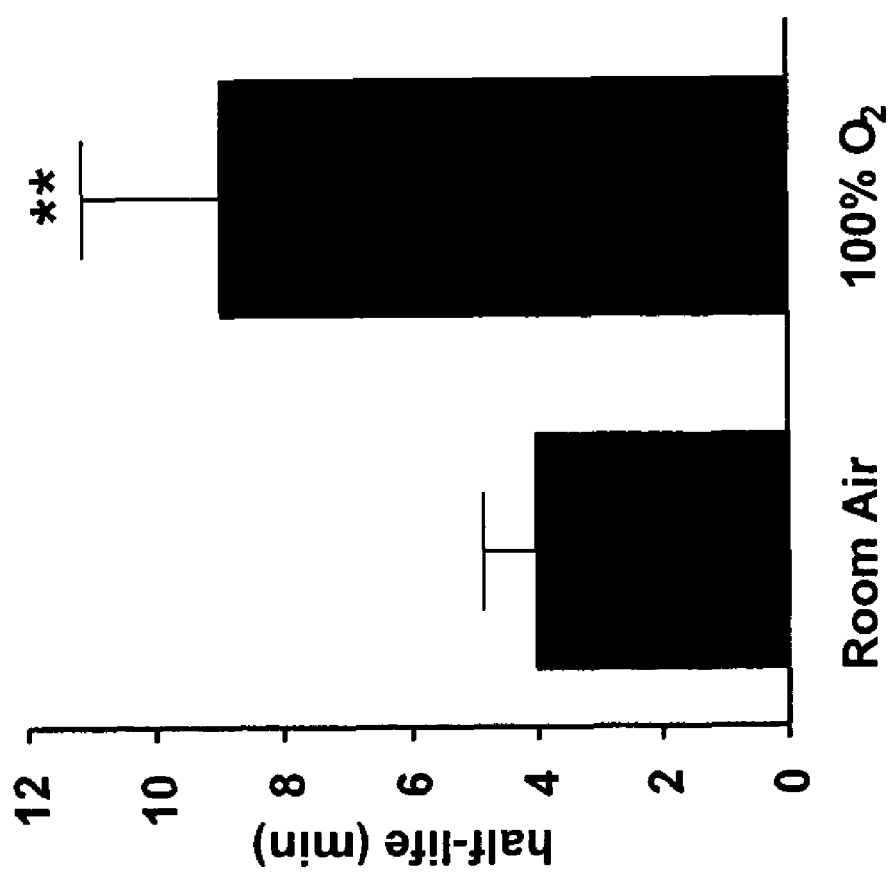
FIG. 2 is a bar graph depicting stabilization of the SNO moiety on plasma SNO-Hb by hyperoxic breathing in vivo. The concentration of SNO proteins was determined over time in the plasma of rats following i.v. infusion of SNO-Hb. The half-life of SNO-Hb is shown for rats breathing room air or 100% $O_2$. (N=5). **$p<0.01$ (Student's t test).

Due to low concentration (about 6.5 μmol/L) and alteration in the tetramer/dimer ratio as a function of concentration and $O_2$ saturation (dimer/tetramer equilibrium is 1000-fold lower in deoxy-Hb), it was not possible to directly measure the oxygen saturation of exogenous Hbs. Instead, plasma SNO-Hb concentration versus time following infusion using a DAF-2 assay was measured. The fitting of individual experimental data with exponential decay curves ($R^2$=0.87±0.05 and 0.901±0.03 for normoxic and hyperoxic conditions, respectively) revealed a 2-fold increase in the half-life of the S-nitrosyl group in SNO-Hb in the plasma of hyperoxic versus normoxic rats (see FIG. 2, p<0.01; Student's t test). No influence of $O_2$ on the rate of SNO-Hb protein clearance was observed. Spectrophotometric measurements revealed that hyperoxia did not affect the rate of protein clearance during the period of the experiments (half-life about 30 minutes, independent of $O_2$ supply). Thus, these data suggest that the effects of $O_2$ are mediated by an allosteric mechanism that promotes the R structure.

Figures 3A, 3B:
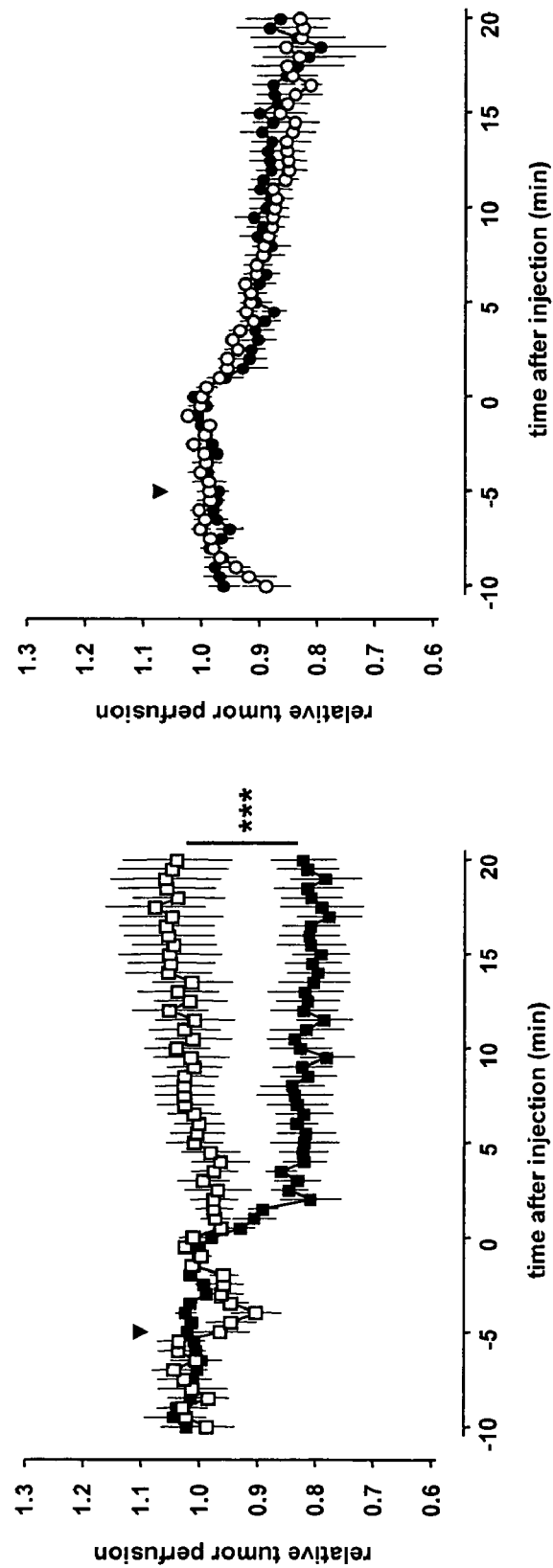
FIGS. 3A and 3B depict selective modulation of the effects of SNO-Hb on tumor perfusion during oxygen breathing. Changes in tumor perfusion were determined by inserting Laser Doppler probes into rat tumors.

The effects of hyperoxia alone on tumor and muscle perfusion ranged from a transient decrease that resumed within 5 minutes (i.e., before drug infusion) to no change. As expected from these observations, hyperoxia abolished the reduction in tumor perfusion that was observed after i.v. infusion of SNO-Hb in normoxic rats (see FIG. 3A, p<0.005; two-way ANOVA). In contrast to SNO-Hb, native Hb reduced tumor perfusion independently of $O_2$ supply (see FIG. 3B, p>0.05; two-way ANOVA).

Example 3

Hyperoxia Unmasks the Systemic Pressor Activity of Cell-Free SNO-Hb

Figure 4:
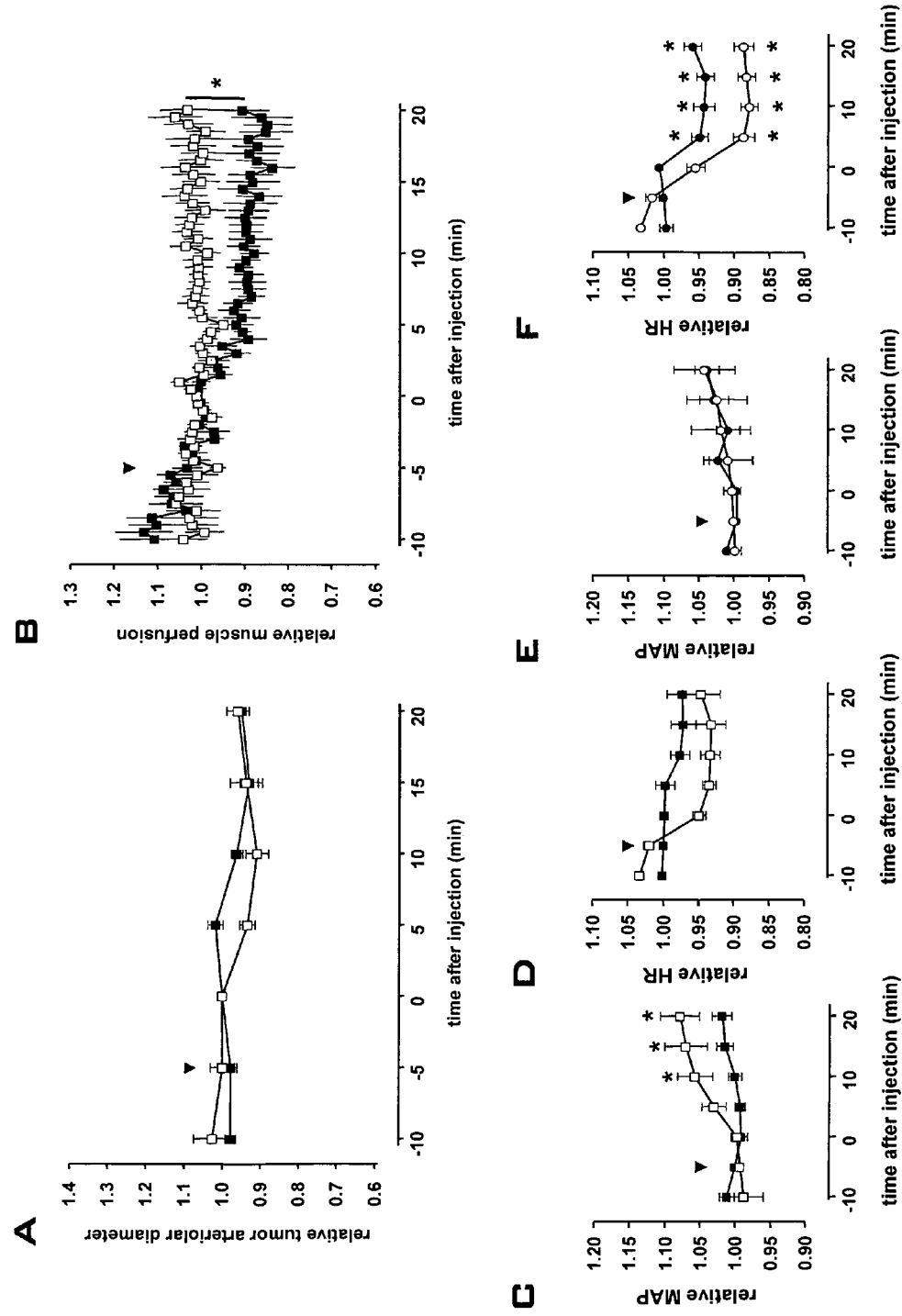
FIGS. 4A-4F are plots depicting an unmasking of systemic pressor activity of plasma SNO-Hb in rats breathing room air or 100% oxygen. SNO-Hb or oxy-Hb was infused i.v. into rats at t=0. Where indicated, rats breathed 100% $O_2$ from t=−5 minutes (arrowheads) until the end of the experiment.

In order to identify the relative contribution of changes in vascular activity versus systemic hemodynamics in the tumor perfusion response to SNO-Hb, i.v. infusion of SNO-Hb induced no significant change in the diameter of feeding arterioles in normoxic or hyperoxic rats as determined by window chamber experiments (see FIG. 4A, p>0.05; two-way ANOVA). Hyperoxia alone had no vascular effect (compare t=−5 to t=0 in FIG. 4A, white boxes). Interestingly, in the same rats, it was simultaneously documented that SNO-Hb induced a potent decrease in tumor perfusion in normoxic animals, and that this decrease was prevented in hyperoxic rats. Thus, these results were identical to what was observed in flank tumors (see FIG. 3A).

Changes in tumor blood flow paralleled changes in the perfusion of the leg quadriceps muscle: the decrease in muscle blood flow after delivery of SNO-Hb under normoxia was prevented under hyperoxia (see FIG. 4B, p<0.05; two-way ANOVA). In contrast, hyperoxia did not modify the effect of oxy-Hb in muscles.

Together, these observations suggested that SNO-Hb might indirectly modulate tumor perfusion in an $O_2$-dependent manner as a consequence of changes in mean arterial pressure (MAP) and/or the heart rate (HR). No change in MAP (FIG. 4C) or HR (FIG. 4D) was observed when SNO-Hb was infused i.v. in normoxic animals (Student's t test versus values at t=0). However, under hyperoxia, a significant increase in the MAP was measured as soon as 10 minutes after the infusion of SNO-Hb i.v. (see FIG. 4C, p<0.05 from t=+10 to t=+20 versus value at t=0; Student's t test). There was no significant effect on HR (see FIG. 4D, p>0.05 for all values versus value at t=0; Student's t test). Interestingly, under the same set of conditions, oxy-Hb had no effect on MAP during normoxia or hyperoxia (see FIG. 4E, p>0.05 for all values versus value at t=0; Student's t test). Also, in contrast to SNO-Hb, oxy-Hb induced bradycardia as soon as 5 minutes after infusion (see FIG. 4D, p<0.05 from t=+5 to t=+20 versus value at t=0; Student's t test), which was more severe in hyperoxic than in normoxic rats. Hyperoxia alone induced no significant changes in MAP (+1%) or HR (−3%; p>0.05, N=19; Student's t test).

Example 4

The Route of Administration Impacts the Pressor Activity of Cell-Free SNO-Hb Whether the physiological difference of blood oxygenation between veins (femoral vein infusion) and arteries (left carotid artery infusion) was sufficient to modulate the pressor activity of SNO-Hb was investigated. In normoxic animals, despite a trend towards preservation of the flow, the decrease in tumor perfusion after i.a. infusion of SNO-Hb was not significantly different compared to i.v. infusion (see FIG. 5A, p=0.09; two-way ANOVA). However, in contrast to i.v. SNO-Hb, the pressor activity of i.a. SNO-Hb was not altered when this experiment was repeated in hyperoxic rats (p>0.05 versus SNO-Hb i.a. room air; two-way ANOVA). The lack of $O_2$ dependence contrasted with the strong $O_2$-dependent changes in tumor perfusion for i.v. infusions (these curves are provided in FIG. 5A for comparison).

Furthermore, $O_2$ concentration in the breathing gas did not modify the perfusion of the quadriceps muscle when SNO-Hb was delivered i.a. (see FIG. 5B, p>0.05; two-way ANOVA). As with the tumor results, the effects contrasted with the changes observed following i.v. injection (see FIG. 4B). Muscle blood flow remained unaltered after i.a. infusion of SNO-Hb, independently of $O_2$ delivery (see FIG. 5B).

Figure 5:
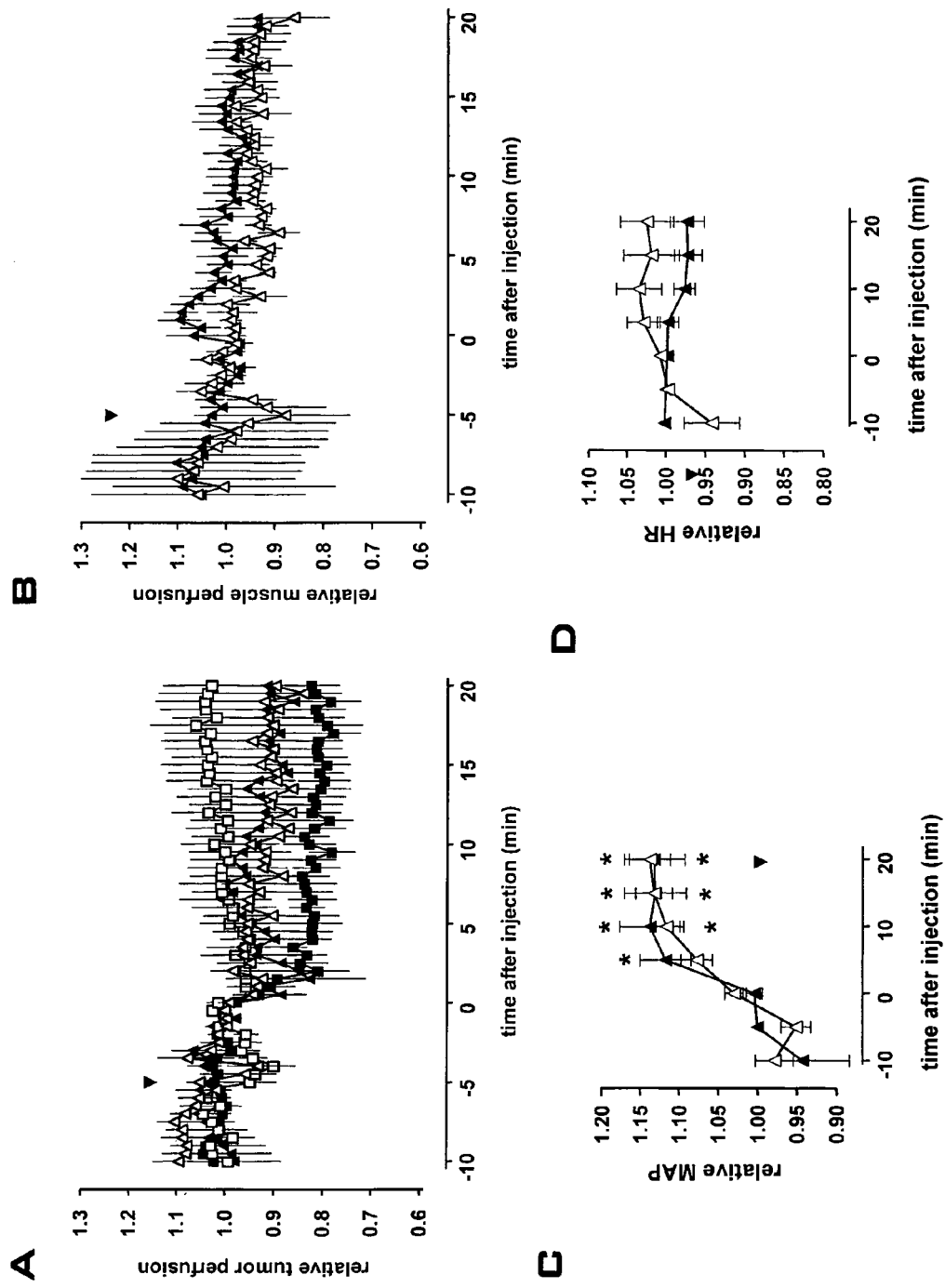
FIGS. 5A-5D are plots depicting the preservation of the pressor activity of SNO-Hb by intra-arterial infusion, which also accounts for loss of $O_2$-dependence. SNO-Hb was infused i.v. or i.a. in rats at t=0. Where indicated, rats breathed $O_2$ from t=−5 minutes (arrowheads).

MAP was highly sensitive to SNO-Hb provided i.a.; a significant increase in MAP as soon as 5 minutes and 10 minutes after drug delivery to normoxic and hyperoxic rats, respectively was observed (see FIG. 5C, p<0.05 versus value at t=0; Student's t test). The degree of hypertension, however, was unaffected by blood $pO_2$. In the same set of experiments, HR remained unchanged (see FIG. 5D). In control experiments, i.a. and i.v. infusion of albumin (used to monitor volume effects on the baroreceptor) did not induce any significant or differential change in tumor perfusion, MAP, or HR of tumor-bearing rats (all p>0.05 for albumin i.a. versus albumin i.v.; two-way ANOVA).

Example 5

Breathing ENO in Pure Oxygen Increases Tumor Perfusion

Tumors were implanted in rats as described hereinabove, and the rats were set up to breathe either 100% $O_2$, 100% $O_2$ plus 100 parts per million ethyl nitrite (ENO), normal room air, or normal room air plus 100 ppm ENO. $pO_2$ was monitored in the tumor or in quadriceps muscle from 30 minutes before the administration of the 100% $O_2$/100% $O_2$ plus 100 ppm ENO/room air/room air plus 100 ppm ENO, during 30 minutes of breathing of the gases, and for 30 minutes after the administered gas supply was removed. The results of these experiments are presented in FIGS. 6A through 6D.

Figure 6D:
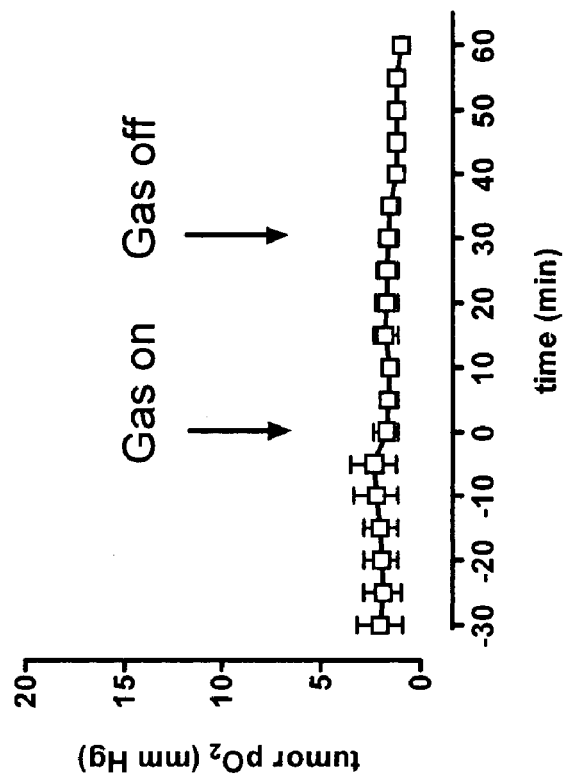
Figure 6C:
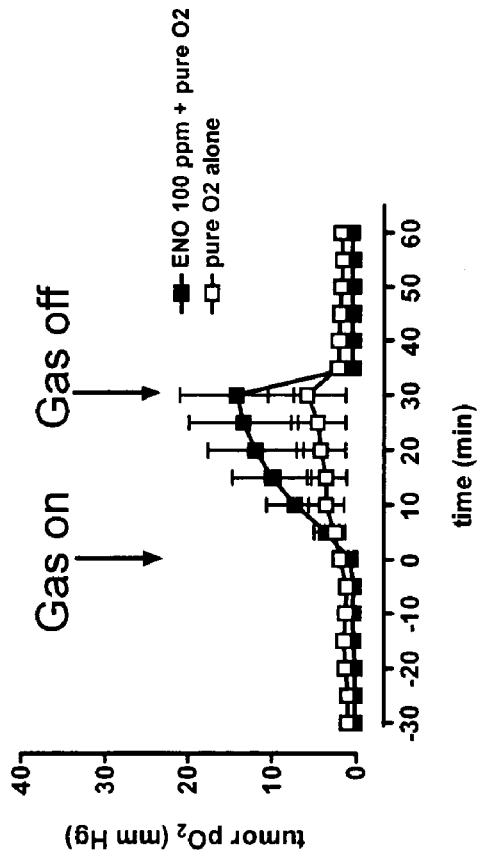

As shown in FIG. 6A, $pO_2$ in quadriceps muscle increased rapidly when the 100% $O_2$ or 100% $O_2$ plus 100 ppm ENO was administered, and quickly returned to baseline when the breathing gas was turned off. As shown in FIG. 6B, this effect was not seen in rats breathing room air plus ENO. Measurements of $pO_2$ in tumors before, during, and after breathing 100% $O_2$ or 100% $O_2$ plus 100 parts per million ENO also showed an increase in $pO_2$ in tumors upon administration of the hyperoxic gas plus ENO, although the increase in $pO_2$ in rats breathing 100% $O_2$ alone was insufficient to raise the $pO_2$ to above 10 mm Hg (see FIG. 6C). FIG. 6D shows that $pO_2$ remained largely unchanged in tumors in rats breathing room air plus 100 ppm ENO changes in $pO_2$. It is interesting to note that in rats breathing 100 ppm ENO plus 100% $O_2$, the $pO_2$ increased from less than 10 mm Hg to greater than 10 mm Hg, but the same increase was not seen in tumors of rats breathing ENO under normoxic conditions.

Example 6

Tumor Growth Delay After 100% Oxygen Plus ENO in Conjunction with Radiation

Tumors were implanted in rats as described hereinabove, and the tumors were irradiated daily with 2 Gy of irradiation on days 0-4. Relative tumor volumes were determined daily from day 0 to day 18 in rats that breathed room air (N=4), 100% $O_2$ (N=4), or 100 ppm ENO plus 100% $O_2$. As a control, relative tumor volumes for rats that breathed room air (N=3) and were not treated with radiation were also determined.

Figure 7:
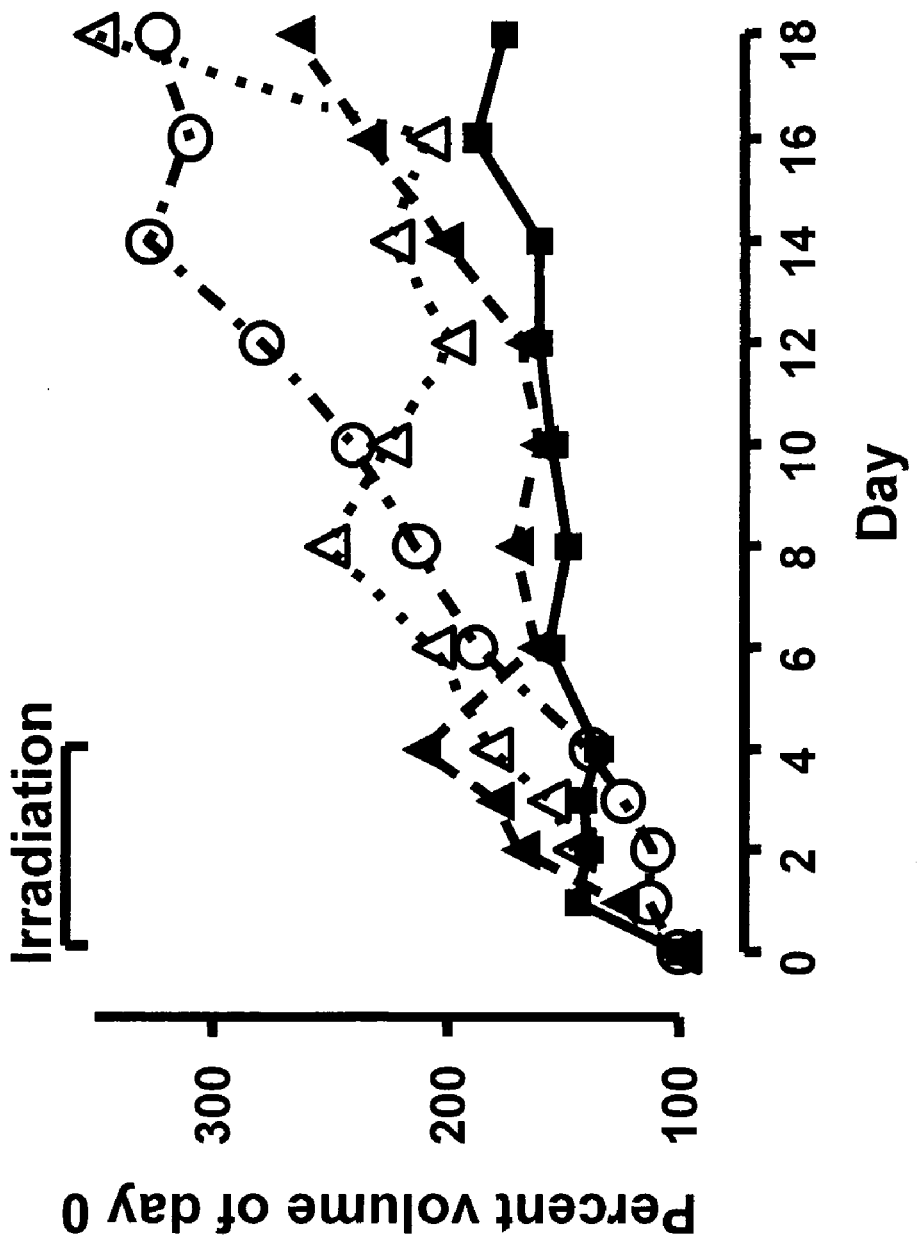
FIG. 7 is a graph depicting tumor growth delay in rats breathing 100 ppm ENO plus 100% $O_2$ after treatment with radiation. Tumors implanted in rats were irradiated daily with 2 Gy of irradiation on days 0-4. Relative tumor volumes were determined on the indicated days in rats that breathed room air (Δ, N=4), 100 $O_2$ (▲, N=4), or 100 ppm ENO plus 100% $O_2$ (■). Also included are relative tumor volumes for rats that breathed room air (○, N=3) and were not treated with radiation.

The results are presented in FIG. 7. As can be seen, irradiated tumors grew more slowly in rats that breathed 100 ppm ENO plus 100% $O_2$ (■) than they did in rats that breathed 100% $O_2$ (▲), rats that breathed room air alone (Δ), or non-irradiated tumors in rats that breathed room air (○).

Discussion of Examples 1-6

S-nitrosylated Hb, when administered i.v. concomitantly with oxygen breathing, is capable of maintaining tumor perfusion (i.e., it counteracts the vasoconstrictive effects of both stroma-free Hb itself and oxygen).

The presently disclosed subject matter thus relates in some embodiments to creating S-nitrosylated hemoglobin in situ in the red blood cell, which yields the same effect, but without the concomitant difficulties of dealing with a stroma-free Hb. To examine this concept, stroma-free hemoglobins, in the form of oxy-Hb and SNO-Hb were administered to tumor bearing rats during air and oxygen breathing, while tumor blood flow was simultaneously monitored.

It was observed that i.v. infusion of human cell-free oxy-Hb and SNO-Hb influenced muscle perfusion in the quadriceps of rats breathing room air (normoxia). SNO-Hb decreased muscle perfusion more than oxy-Hb when compared to albumin (see FIG. 1A). Studies were also performed in tumor-bearing rats, where the tumors were transplanted to the flanks. The pharmacological effects of these molecules in tumors grown in the flank of normoxic rats were determined. In contrast to albumin, oxy-Hb induced a rapid and sustained decrease in tumor blood flow (see FIG. 1B). Unexpectedly, i.v. infusion of SNO-Hb also produced such a decrease (see FIG. 1C). Thus, the reductions in flow caused by oxy-Hb and SNO-Hb were not different. However, the effects of the two Hb species were quite different from the small increase in tumor perfusion that was observed following albumin or SNO-albumin infusion i.v. (see FIGS. 1B and 1C).

The effects of the two hemoglobin species were quite different when animals were breathing oxygen during and following the infusion of the hemoglobin solutions. Hyperoxia prolonged the half-life and modulated the vasoactivity of cell-free SNO-Hb. Blood gas measurements showed that 100% $O_2$ breathing induces significant increases in venous and arteriolar blood $pO_2$, $pCO_2$, and endogenous Hb oxygen saturation. Changes in Hb saturation were found to be identical in femoral vein and tumor venules; it is less pronounced in tumor-feeding arterioles versus femoral artery, as expected from blood deoxygenation along the arterial tree and at the tumor margin (see Table 1).

The half life of the S-nitrosyl group of SNO-Hb was determined using the DAF-2 assay. Fitting of individual experimental curves with exponential decay curves ($R^2$=0.87±0.05 and 0.90±0.03 for normoxic and hyperoxic conditions, respectively) revealed a 2-fold increase in the half-life of the S-nitrosyl group on SNO-Hb in the plasma of hyperoxic versus normoxic rats (see FIG. 2). Of note, $O_2$ did not influence on the rate of SNO-Hb protein clearance. The effects of hyperoxia alone on tumor and muscle perfusion ranged from a transient decrease that resumed within 5 minutes (i.e., before drug infusion) to no change. As expected from these observations hyperoxia abolished the reduction in tumor perfusion after i.v. infusion of SNO-Hb in normoxic rats (see FIG. 3A). In contrast to SNO-Hb, oxy-Hb reduced tumor perfusion independently of $O_2$ supply (see FIG. 3B).

A further discovery showed that hyperoxic gas breathing unmasked a systemic pressor activity of cell-free SNO-Hb. In window chambers, i.v. infusion of SNO-Hb induced no change in diameter of tumor-feeding arterioles in normoxic or hyperoxic rats (see FIG. 4A). Additionally, hyperoxia alone had no discernable effect on arteriolar diameter. In spite of the lack of tumor arteriolar effects, SNO-Hb potently induced a decrease in tumor perfusion in normoxic animals, and this decrease was prevented in hyperoxic ones. These results were identical to what was observed in flank tumors (see FIG. 3A). The lack of change in arteriolar diameter in tumor arterioles suggested that the vasoactive properties of SNO-Hb were either occurring upstream or that systemic effects dominated the change in flow within the tumors. Results in muscle helped to discern the underlying mechanism.

Changes in the tumor blood flow were paralleled by changes in the perfusion of the leg quadriceps muscle: a decrease in muscle blood flow after delivery of SNO-Hb under normoxia was prevented under hyperoxia (see FIG. 4B). In contrast, hyperoxia did not modify the effect of oxy-Hb in muscle perfusion. Altogether, these observations led to the conclusion that SNO-Hb indirectly modulated tumor perfusion as a consequence of changes in the mean arterial pressure (MAP) and/or the heart rate (HR), in an $O_2$-dependent way. No changes in MAP (see FIG. 4C) or HR (see FIG. 4D) were observed when SNO-Hb was infused i.v. in normoxic animals. However, under hyperoxia, a significant increase in the MAP as soon as 10 minutes after the infusion of SNO-Hb i.v. was observed (see FIG. 4C). There was no significant effect on HR (FIG. 4D). Interestingly, under the same conditions, oxy-Hb had no effect on MAP during normoxia or hyperoxia (see FIG. 4E). Moreover, in contrast to SNO-Hb, oxy-Hb induced bradycardia as soon as 5 minutes after infusion (see FIG. 4D), which was more severe in hyperoxic than in normoxic rats. Hyperoxia alone induced no significant changes in MAP (+1%) or HR (−3%).

The $O_2$ dependency of the bioactivity of SNO-Hb prompted determination of whether the physiological difference of blood oxygenation between veins (femoral vein infusion) and arteries (left carotid artery infusion) was sufficient to modulate the vasoactive properties of SNO-Hb. In normoxic animals, i.a. infusion of SNO-Hb induced a less dramatic decrease in tumor perfusion than when the drug was delivered i.v. (see FIG. 5A). In contrast to the i.v. case, the vasoactive effects of i.a. SNO-Hb were not modified when this experiment is repeated in hyperoxic rats. The lack of $O_2$ dependency contrasted with the strong $O_2$-dependent changes in tumor perfusion for i.v. infusions (these curves are provided in FIG. 5A for comparison). Moreover, $O_2$ supply did not modify the perfusion of the quadriceps muscle when SNO-Hb is delivered i.a. (see FIG. 5B). As with the tumor results, the effects contrasted with the changes that were observed following i.v. injection (see FIG. 4B). Muscle blood flow remained unaltered after i.a. infusion of SNO-Hb, independently of $O_2$ delivery (see FIG. 5B). However, MAP was highly sensitive to SNO-Hb i.a.: a significant increase in MAP was observed 5-10 minutes after SNO-Hb delivery to normoxic and hyperoxic rats, respectively (see FIG. 5C). The degree of hypertension, however, was unaffected by blood $pO_2$. In the same set of experiments, HR remained unchanged (see FIG. 5D).

These data revealed interesting biological properties of Hb in the plasma. First, the effects of SNO-Hb were dependent on blood oxygenation (biologically relevant range) while the effects of oxy-Hb were not. Second, when delivered in oxygenated blood, SNO-Hb affected the central control of hemodynamics.

During hyperoxia, SNO-Hb stabilization occurred in the venous circulation. Evidence for this came from the fact that SNO-Hb bioactivity was identical following hyperoxic i.v. and normoxic intraarterial (i.a.) infusions. Moreover, hyperoxia combined with i.a. infusion did not further modulate the effects of SNO-Hb. Changes correlated with increased blood $pO_2$ but not $pCO_2$. Hence, physiologically oxygenated blood at the site of delivery was sufficient to prolong SNO-Hb bioactivity with maximal efficiency.

SNO release in oxygenated plasma cannot be completely prevented, however. Indeed, i.a. infusion during normoxia and i.v. and i.a. infusions during hyperoxia demonstrated a central pressor activity of SNO-Hb whereas oxy-Hb (hyperoxia, i.v.) did not show this effect. Baroreceptor activity opposes increases in MAP and resistance to flow by inhibiting the sympathetic nerve activity. At physiological concentrations, hemodynamic responses to oxy-Hb apparently activated the baroreceptor that buffers changes in MAP by decreasing HR. The observation that SNO-Hb in oxygenated blood raised the MAP without altering perfusion or HR was therefore unexpected. Comparison indicated that the systemic pressor activity of SNO-Hb resulted from a direct inhibition of the baroreceptor reflex.

NO is well known, as a neurotransmitter, to regulate baroreceptor activity through sympathetic afferent nerve fibers (Paton et al., 2001). In contrast, circulating NO donors have no direct inhibitory action on the baroreceptor unless delivered at high concentration (>100 µmol/L) directly into the carotid sinus, and the baroreceptor activity recovers spontaneously within seconds. This contrasts with the prolonged inhibition of the baroreceptor disclosed herein in the presence of SNO-Hb. Unlike classical NO activity, SNO-Hb bioactivity was mediated by NO-related species distinct from NO itself (e.g., small molecular weight SNO), and these species would then have different effects than NO gas.

SNO conjugation successfully overcame the pressor activity of micromolar concentrations of Hb in hypoxic (tumors) and normoxic tissues. This activity required injection in hyperoxygenated venous blood or normoxic arterial blood. Under such circumstances SNO-Hb was allosterically stabilized. The peripheral effects of SNO-Hb were a composite between central activity (baroreceptor inhibition) and allostery-facilitated activity in the periphery. In contrast, native Hb at concentrations characteristic of hemolytic states had no central pressor effect.

Thus, the presently disclosed subject matter provides improved delivery of oxygen to tumors while preserving perfusion. The combination of improved oxygenation and perfusion maintenance can translate into increased tumor radioresponsiveness and chemoresponsiveness. Increased levels of SNO-Hb in the peripheral circulation can prevent the vasoactive effects of hyperoxic gases, thereby maintaining and even improving perfusion and oxygen delivery to hypoxic tumor regions. Unloading of SNO from Hb in the more hypoxic regions of a tumor can also serve to radiosensitize and/or chemosensitize such regions. In some embodiments, the presently disclosed subject matter is based at least in part on modifying endogenous stores of SNO-Hb. In some embodiments, the presently disclosed subject matter provides S-nitrosylated-Hb directly to the subject.

Vasoconstriction remains a major limitation in the clinical use of Hb-based blood substitutes. Cell-free Hb preparations are devoid of the SNO that normally serves to counter their vasoconstrictive effects in vivo. Disclosed herein is the discovery that SNO reconstitution of Hb can reverse the vasoconstrictor activity of oxy-Hb, and further that SNO-Hb can be manipulated allosterically to maximize $O_2$ delivery. In rats breathing room air (normoxia), SNO-Hb induced a greater decrease in tissue perfusion than native Hb (see FIG. 1A and Table 2). These results suggested that oxy-Hb and SNO-Hb operated by different mechanisms. While the effects of oxy- Hb could be readily explained by NO scavenging (the "oxyhemoglobin," or met-Hb-forming reaction), those of SNO-Hb were consistent with other NO donors, which paradoxically also decrease tissue perfusion. NO-mediated dilation of healthy blood vessels upstream of tumors creates shunts that divert blood away from the tumors (vascular steal). By raising the concentration of the inhaled $O_2$, SNO-Hb bioactivity can be targeted to more distally blood vessels, and elicits improvements in tumor blood flow.

TABLE 2

Hemodynamic Properties of Cell-free Human SNO-Hb and Oxy-Hb

| | | | TUMOR | | SYSTEMIC | | |
|---|---|---|---|---|---|---|---|
| | | | perfusion | vascular diameter | perfusion | MAP | HR |
| SNO-Hb | IV | Room air | ↓* | 0 | ↓ | 0 | 0 |
| | | 100% $O_2$ | 0 | 0 | 0 | ↑ | 0 |
| | IA | Room air | 0 | nd | 0 | ↑ | 0 |
| | | 100% $O_2$ | 0 | nd | 0 | ↑ | 0 |
| Oxy-HB | IV | Room air | ↓ | nd | ↓ | 0 | 0/↓ |
| | | 100% $O_2$ | ↓ | nd | ↓ | 0 | 0/↓ |

*refers to changes versus values before treatment:
0, unchanged;
↓, decreased;
↑, increased;
nd, not determined.
SNO-Hb, human S-nitrosohemoglobin;
oxy-Hb, human oxyhemoglobin;
IV, intravenous infusion;
IA, intra-arterial infusion;
MAP, mean arterial pressure;
HR, heart rate.

To further test oxygen-dependent regulation of NO release, the activity of cell-free SNO-Hb versus native Hb in tumors was investigated. The well-characterized R3230Ac rat mammary tumor model was employed to observe low but biologically significant $pO_2$ conditions. In normoxic rats, SNO-Hb i.v. lowered perfusion in tumors to the same extent as in muscles (see Table 2). In tumors, oxy Hb exhibited a similar decrease in perfusion, while albumin (and to a similar degree SNO-albumin) tended to increase perfusion slightly (see FIGS. 1B and 1C).

Interestingly, the SNO-Hb-induced decrease in tumor perfusion was not associated with tumor-feeding vessel constriction or changes in MAP or HR (see Table 2). While it is not desired to be bound by any particular theory of operation, it appears that the observations can be attributed to: (1) vasoconstriction (NO scavenging) of microvessels within the tumor; and/or (2) vasodilation (SNO release) of vessels in parallel tissues that creates a vascular steal. Because of ongoing angiogenesis, most vessels downstream of feeding arterioles in fast-growing rodent tumors lack structural elements for vasoactivity, and they lack functional endothelial NO synthase. Hence, during normoxia, SNO-Hb i.v. must decrease tumor perfusion through vascular steal. This is consistent with the previous observation that, although oxy-Hb provoked a decrease in healthy muscle perfusion (as expected from a NO scavenger), it increased perfusion in muscle surrounding the R3230AC tumor (a NO donor-like response) consistent with a steal effect.

To gain further mechanistic insight, whether manipulation of blood oxygenation would impact SNO-Hb bioactivity was tested. Normobaric 100% oxygen breathing (hyperoxia) induced a significant increase in venous and arteriolar $pO_2$ (see Table 1). Although the delivery of pure oxygen sometimes reduced tumor and muscle perfusion (see FIGS. 3A, 3B, 5A, and 5B between t=−5 and t=0), this effect was transient and returned to baseline within less than 5 minutes. Thus, the vasoactive properties of oxygen per se did not affect the response to SNO-Hb or oxy-Hb. Upon i.v. infusion in hyperoxic animals, SNO modified Hb successfully opposed the reduction in perfusion created by Hb in tumors (compare FIGS. 3A and 3B). Increases in MAP were seen in response to SNO-Hb during 100% $O_2$ breathing, but there was no change in tumor/muscle perfusion or HR (see Table 2). By comparison, the reduction in tumor perfusion by native Hb remained unaffected by hyperoxia (see FIG. 3B). This is likely accounted for by lowered systemic perfusion and/or bradycardia, not by changes in MAP (see Table 2).

Hb dissociation from tetramers to dimers depends on Hb concentration and oxygen tension, and NO release from dimers is unresponsive to allosteric effectors (e.g., $O_2$). Assuming a plasma concentration of about 6.5 μmol/L, about 35% of SNO-Hb would be tetramers ($K_D$ for R and T conformers are 3 μmol/L and 3 nmol/L, respectively) at room air and the amount would increase precipitously as $O_2$ tension declines—the majority would be tetramers at tissue $pO_2$. Is there enough tetrameric SNO-Hb to sense oxygen and regulate NO delivery? Evidently yes, as a finely tuned regulation of SNO-Hb bioactivity by oxygen tension (NO release depends on local $pO_2$) that contrasted with the $O_2$-independent behavior of oxy-Hb was observed. That the plasma half-life of SNO on Hb was more than doubled during hyperoxia while protein clearance remained unaffected was also observed. Thus, the prolonged half-life of SNO bound to equally stable Hb proteins supported the assertion that SNO release by SNO-Hb is disfavored under hyperoxia. Collectively, these data provided a definitive demonstration of allosteric regulation by $O_2$ of NO delivery from SNO-Hb.

During hyperoxia, SNO-Hb is greatly stabilized, surviving arteriovenous transit. SNO-Hb bioactivity was thus indistinguishable following hyperoxic i.v. and normoxic i.a. infusions (see Table 2). To address a point of confusion, it is noted that SNO-Hb will exert activity at both high and low $pO_2$ but that this activity will be potentiated at low $pO_2$. Effects will therefore manifest locally. Consistent with this interpretation, hyperoxia had no effect on i.a. infusions of SNO-Hb but markedly altered i.v. responses (see Table 1).

On close inspection, the data disclosed herein unravel a central effect of SNO-Hb on control of hemodynamics. An increase in MAP was observed following i.a. infusion during normoxia, and both i.v. and i.a. infusions during hyperoxia. Native Hb (hyperoxia, i.v.) did not produce increases in MAP (see Table 2) under any condition. Baroreceptor activity opposes increases in MAP and resistance to flow. Native Hb activated the baroreceptor, which opposed changes in MAP by decreasing the HR. In contrast, strikingly, SNO-Hb raised the MAP without altering perfusion (in the organs that were monitored) or HR. The systemic pressor activity of SNO-Hb resulted from a direct inhibition of the baroreceptor reflex.

Thus, SNO-Hb activity in hyperbaric hyperoxia is sufficient to inhibit the baroreceptor. As a neurotransmitter, NO is known to regulate baroreceptor activity through sympathetic afferent nerve fibers. Exogenous NO has an inhibitory action on the baroreceptor, albeit only at high concentrations, and under such circumstances that the baroreceptor activity recovers within seconds. Unlike classical NO activity, SNO-Hb bioactivity is mediated by species distinct from NO· itself (e.g., low-mass SNOs). It is noteworthy that other endogenous S-nitrosothiols such as SNO-cysteine can suppress baroreceptor activity independently of cGMP generation (the mediator of classical nitrovasodilator activity). Stereoselective recognition sites in the baroreceptor vasculature could mediate baroreceptor inhibition by S-nitrosylated species such as SNO-cysteine and SNO-Hb.

In conclusion, disclosed herein is the observation that SNO reconstitution of Hb successfully overcame the reduction in tumor perfusion created by Hb itself. This activity involved the allosteric control of NO release by $O_2$. The hemodynamic effects of SNO-Hb were a composite of central activity (baroreceptor inhibition) and allostery-facilitated NO release in the peripheral circulation. In contrast, native Hb at concentrations characteristic of hemolytic states had no central pressor effect. These results are summarized in Table 3.

TABLE 3

Bioactivity of Cell-free SNO-Hb and Oxy-Hb.

| | Vascular $pO_2$ at injection site | NO-related chemical fate | Peripheral effect | Baroreceptor effect |
|---|---|---|---|---|
| SNO-Hb ↓↑ | low | Met-Hb + iron-nitrosyl Hb | vasoconstriction | none |
| | high | SNO-Hb | vasodilation° | inhibition |
| Oxy-Hb | any | Met-Hb + iron-nitrosyl Hb | vasoconstriction | none |

SNO-Hb, S-nitrosohemoglobin;
oxy-Hb, oxyhemoglobin;
NO, nitric oxide;
Met-Hb, methemoglobin.
°Dose-dependent effect.

While the concentration of Hb used was low from the $O_2$ delivery standpoint, it greatly exceeded the concentration of any endogenous NO. In light of the results presented herein, development of safe Hb-based blood substitutes might include approaches that not only preserve Hb allostery (e.g., crosslinking to prevent dissociation into dimers) but also reconstitute SNO content. Reoxygenation of hypoxic tissues might benefit from both the central pressor and blood flow increasing effects elicited by SNO-Hb. Further, the treatment of trauma or septic patients might involve manipulation of SNO-Hb allostery to limit excessive NO release.

Materials and Methods for Examples 7-10

Tumor Implantation, Growth, and Definition of Treatment Size. Cells are grown to 80% confluency in culture dishes and implanted into the flanks of athymic nude mice at a concentration of 1 million cells per animal. The tumor volume is measured starting from the day of palpable appearance. Tumor volume is calculated as volume ($mm^3$) equals (p/6) $xy^2$, with x=longer and y=shorter axis of the tumor (see Baumann et al., 1990). Animals with tumors of a size of 500 $mm^3$, or an average diameter of 10±1 mm, are considered eligible for treatment.

Administration of gas to mice. Gas mixtures are administered over customized face masks using mixture-specific mass flow controllers (provided by NITROX LLC, Durham, N.C., United States of America). Five animals are ventilated at a time using a one-in-five distributor. During all measurements equal body temperature is maintained by placing the animals on metal plates that sit on water-circulated heating pads.

Radiation treatment of tumors. Tumor irradiation is performed in using a clinical linear accelerator. Animals are anesthetized at the site of irradiation using pentobarbital. Flank tumors are exposed using customized animal restrainers. The animal body is shielded using lead blocks.

Measurement of tumor oxygenation using fiber-optic sensors. Tumor oxygenation is measured using the Oxylite system (Oxford Optronix, Oxford, United Kingdom), which is based on probe-based measurements of oxygen-dependent fluorescence quenching and signal detection over fiber-optic cables. The system employs concurrent measurements of tissue temperature using thermocouples.

Example 7

Optimization of ENO Dose

The lowest effective dose (LED) of ENO is determined on FaDu (human hypopharyngeal carcinoma cells, available from the American Type Culture Collection, Manassas, Va., United States of America) tumor xenographs with tumor oxygenation as an endpoint. Separate cohorts of animals are exposed to room air, $O_2$ alone, or $O_2$ supplemented with different concentrations of ENO (e.g., 100 ppm, 75 ppm, 50 ppm, 25 ppm, 10 ppm). Each group includes 15 animals. Oxygenation is measured using the Oxylite system and by histology comparing pimonidazole hypoxic fraction with total vital tissue. The endpoint is the identification of the lowest ENO dose showing improvement in tumor oxygenation equivalent or better than that achieved with a 30 minute continuous exposure of 100 ppm ENO+$O_2$, which as disclosed herein increased tumor $pO_2$ above 10 mmHg. Nitrite/nitrate levels (a follow up product of NO) in the blood of animals treated with the LED are analyzed to assess systemic effects of this dose of ENO. As a surrogate marker of ENO exposure and to validate the mechanistic action of ENO, cGMP levels are also assessed in the tumor.

More particularly, FaDu cells are implanted into athymic nude mice and grown to treatment size. Animals are anesthetized with nembutal, catheterized for re-dosing of anesthesia, and placed on a heated animal restrainer. In order to simulate irradiation conditions, the animals are placed on a clinical irradiator for the duration of the experiment. Two oxygen probes are inserted into different parts of the tumor: one close to the surface, the other at the center of the tumor. A third probe is inserted into the muscle of the opposite hind leg, as a control. Thermocouples are inserted into the tumor and the muscle. Oxygen and temperature values are monitored constantly throughout the experiment. A laser Doppler probe (OxyFlo, Oxford Optronix, Oxford, United Kingdom) is inserted into the tumor to measure changes in tumor blood flow during treatment.

Room air is administered to the animal at a rate of 5 L/minutes via a face mask. After 30 minutes, room air is replaced with an ENO/oxygen gas mixture, administered at the same rate. At the same time, pimonidazole is administered i.p. at a concentration of 20 mg/kg. The animal is allowed to breathe the gas mixture for 60 minutes. Five minutes before sacrificing the animal, Hoechst 33342 (Bisbenzimide, Sigma, St. Louis, Mo., United States of America) is injected i.v.

The tumor is excised and snap frozen in liquid nitrogen. Samples are sectioned and analyzed for pimonidazole hypoxic fraction as outlined hereinbelow. The first ENO dose tested is 25 ppm. Depending on whether this dose is already sufficient not to increase the tumor oxygenation to at least 10 mmHg, continued testing with the next lower (10 ppm) or the next higher (50 ppm) dose is performed. The endpoint of this study is the identification of the lowest effective dose (LED), which is the lowest dose of ENO showing improvement of tumor oxygenation beyond 10 mm Hg.

Five animals out of each group are subjected to treatment as outlined, with the exception that after removal of the tumor, a blood sample is obtained by cardiac puncture from the anesthetized animal. Each blood sample (approx. 500 μl) is mixed 1:5 with a nitrite/nitrate preservation solution (see Dejam et al., 2005). Analysis of nitrite/nitrate is performed. The endpoint tests whether the nitrite/nitrate levels found in the blood plasma of the animals correlated with (and thus are determined by) the administered ENO concentration.

All tumor samples are also analyzed for cGMP content, an intracellular downstream effector of NO. Slices from tumor samples (consecutive to those analyzed for pimonidazole) are pooled into lysis buffer, subjected to extraction, and analyzed for cGMP using an antibody-based commercial method (cGMP BIOTRAK™ enzymeimmunoassay system, Amersham Pharmacia, Piscataway, N.J., United States of America). This allows for direct comparison of cGMP values (indicating the presence of NO) and the extent of pimonidazole hypoxic fraction in the tumors.

Example 8

Determination of Single Dose Radiation Dose Modifying Factor (DMF) for ENO Plus Oxygen The relative value of a radiosensitizer to improve radiation response is quantified by determining the Dose Modifying Factor (DMF). This is determined by establishing the ratio of radiation doses required to cure 50% of tumors for radiation alone divided by the dose required for radiation plus radiosensitizer (see Baumann et al., 1990). Tumor-bearing animals with tumors grown to a specified size range are randomized to receive pre-defined single doses of radiation (that bracket the doses expected to yield between 10 and 90% local tumor control)±ENO+$O_2$ breathing or $O_2$ breathing alone. The ENO dose optimized as in EXAMPLE 7 is used. The radiation dose that leads to a lack of regrowth in 50% of the tumors within the observation period ($TCD_{50}$) for each treatment arm is determined using logistic regression methods. It is expected that the DMF will be greater than one and will be largest for ENO+$O_2$ compared with $O_2$ alone.

More particularly, FaDu tumors are grown in nude mice. Starting from the day of palpable tumor appearance, tumor growth is monitored biweekly using caliper measurements by an investigator who is blinded to the grouping of the animals. When tumors reach treatment size, radiation is applied as a single dose in the range between 15 to 45 Gy, with 5 Gy increments and eight animals per group. Treatment arms include air breathing+irradiation, pure oxygen breathing plus irradiation, and ENO/$O_2$ optimized dose (as determined in EXAMPLE 7) plus irradiation. Gas flow rates are equivalent to those specified in EXAMPLE 7. Muscle $pO_2$ is monitored during radiation treatment using Oxylite probes placed in the muscle of the tumor-free leg to ensure consistency in ENO exposure. After treatment, animals are monitored for tumor regression and regrowth. Animals that show regression are followed for 120 days. Those that do not show regrowth in that time interval are considered to have achieved local tumor control. The different treatment modalities are compared with each other by calculating the $TCD_{50}$. The Dose-Modifying Factor (DMF) is the ratio of the $TCD_{50}$ values of the treatment arms that are compared (see Yaromina et al., 2005). The DMF of ENO/$O_2$ and room air, and ENO/$O_2$ and pure oxygen breathing is determined.

Example 9

Pathological Consequences of Irradiation Administered with and without ENO+Oxygen Breathing To explore the pathologic consequences of ENO/O2 breathing during irradiation (using a dose near the $TCD_{50}$ as determined in EXAMPLE 8), the effect of this treatment on hypoxic fraction, as assessed by hypoxia marker uptake, proliferation and apoptosis rates, percentage of necrotic area, and vascular density is assessed. These parameters are measured, using quantitative immunohistochemistry, at defined time points after radiation treatment.

More particularly, to explore the pathologic consequences of co-treatment of ENO/$O_2$ breathing plus irradiation, the effect of these treatments on the following parameters is determined:

(1) hypoxic fraction, as assessed by hypoxia marker uptake
(2) proliferation and apoptosis rates
(3) percentage of necrotic area
(4) vascular density For these experiments, separate cohorts of animals are studied. Tumors are grown to treatment size and then receive a single radiation dose that is below that required to cure tumors in any of the treatment groups, but that is sufficient to cause growth delay by radiation alone. Out of each treatment group (room air, pure oxygen, ENO best dose, untreated) 12 animals are removed after treatment in a time dependent manner: animals are removed in triplicate at 0, 24, 48, and 72 hours after treatment, respectively. All of these animals are injected with pimonidazole at 6 μl/g from a stock solution of 10 mg/mL 1.5 hours before sacrifice. Hoechst 33342 is injected into each animal's tail vein 5 minutes before tumor removal to serve as a perfusion marker.

Tumors are cryosectioned and stained for the degree of hypoxia (pimonidazole), proliferation activity (KI67), apoptosis (DNA strand breakage, TUNEL), CD31 for microvessel density, perfused microvessel density (co-localization of Hoechst 33342 and CD31), and necrosis (based on histologic assessment of H/E stained tissues) as follows:

Pimonidazole Hypoxic Fraction. Pimonidazole is a well-established immunohistochemical marker of tumor hypoxia. Tumors are cryosectioned and sections fixed and stained with fluorescently-labeled antibodies. Slides are scanned using a fluorescence microscope equipped with a computerized stage and shutter. After fluorescence imaging, the same sections are stained with hematoxylin/eosin to determine vital tumor areas. The endpoint of these measurements are the differences in the pimo-positive vs. overall vital tumor area between treatment groups 2 and 1 as shown in Table 4.

TABLE 4

Treatment Groups and Dosing Schedule for EXAMPLE 8

| # | Treatment group | Radiation dose (Gy) | ENO | Oxygen | Nitrogen | # mice |
|---|---|---|---|---|---|---|
| 1 | ENO (LED) | 25 | TBD | TBD | TBD | 12 |
| 2 | Pure oxygen | 25 | — | 4.5 | 0.5 | 12 |
| 3 | Room air | 25 | — | 1.05 | 3.95 | 12 |

TABLE 4-continued

Treatment Groups and Dosing Schedule for EXAMPLE 8

| # | Treatment group | Radiation dose (Gy) | Flow rate (L/minutes) | | | # mice |
|---|---|---|---|---|---|---|
| | | | ENO | Oxygen | Nitrogen | |
| 4 | No treatment | — | — | — | — | 12 |

Percentages of vital tissue that are positively stained for pimonidazole are compared between the treatment groups. Differences between groups are tested for significance using standard ANOVA methods. Tumors are cryosliced and sections are fixed and stained with fluorescence-labeled antibodies. Slides are scanned using a fluorescence microscope with computerized stage and shutter, and, after imaging, stained and imaged for hematoxylin/eosin to determine vital tumor areas.

The KI67 proliferation index. The nuclear antigen KI67 is detected using established immunohistochemical protocols involving a polyclonal primary and fluorescently-labeled secondary antibody and a Hoechst 33342 counterstain to identify cell nuclei. The KI67 positive area is evaluated using a 16 bit microscope camera and grayscale analysis as described in Moeller et al., 2005.

Apoptosis. Detection of the percentage of apoptotic cells by terminal transferase dUTP nick end labeling (TUNEL) is performed using established protocols (see e.g., Le et al., 2005). The signal is visualized using fluorescence microscopy and evaluated as described hereinabove.

Quantification of microvessel density. Tumor microvessels are detected by CD31 staining as described in Peeters et al., 2004, followed by fluorescence-based detection of the primary antibody. The slides are scanned under a fluorescence microscope with a motorized traveling stage. Images are background-corrected and filtered and microvessel density is determined in selected areas using particle counts and histogram analysis.

Perfused microvessel density. This is determined by examining the percentage of CD31 positive vessels that exhibit perivascular Hoechst 33342 staining.

Quantification of percent necrosis. This is determined using image analysis software. Total tumor area is identified and quantified in terms of $mm^2$ surface area. The percentage area that is necrotic is determined by using planimetry to outline necrotic regions. The percentage of necrotic area is calculated as the ratio of the total tumor area divided into the area of tissue that is necrotic. Areas of tissue that contain artifacts, such as tearing during sectioning, are subtracted from the overall tumor area.

Example 10

Ability of Optimized ENO+Oxygen Dose to Improve Tumor Oxygenation and Reduce Hypoxia Measurements of oxygen concentration and perfusion are made prior to and during breathing of ENO+oxygen, oxygen alone, or air alone. Using dose finding experiments, the degree of variability of oxygenation response to ENO+oxygen breathing among tumors with different metabolic capabilities is assessed.

In order to assess the heterogeneity of tumor response to ENO+oxygen breathing, FaDu tumors are compared to SiHa (human cervical cancer) and WiDr (human colorectal cancer) xenografts. These tumor lines have been chosen in part because that these tumors differ in their intrinsic rates of oxygen consumption, and differences in oxygen consumption are likely to have an impact on the efficiency of strategies to deliver oxygen to the tumor. Measurements of tumor oxygenation are performed with the Oxford Optronix fluorescence quenching probe paralleled by Laser Doppler measurements (OxyFlo, Oxford Optronix, Oxford, United Kingdom), providing information on whether changes in oxygenation are related to tumor blood flow changes. Dose finding experiments are performed on SiHa and WiDr tumors as described in EXAMPLE 7. The ENO LED identified for FaDu tumors in EXAMPLE 7 is used as a starting point, and increases or decreases from this dose in 25 ppm increments depending on whether or not oxygenation response is lower or higher in FaDu tumors, are employed (see e.g., an exemplary dosing schedule presented in Table 5). The oxygenation effect in FaDu tumors is also confirmed.

TABLE 5

Treatment Groups and Dosing Schedule

| ENO | Flow rate (L/minutes) | | | # mice | # mice |
|---|---|---|---|---|---|
| $LED_{FaDu}$ +/− ENO | | Oxygen | Nitrogen | WiDr | SiHa |
| 100 ppm | TBD | 4.5 | — | 10 | 10 |
| 75 ppm | TBD | 4.5 | TBD | 10 | 10 |
| 50 ppm | TBD | 4.5 | TBD | 10 | 10 |
| 25 ppm | TBD | 4.5 | TBD | 10 | 10 |
| 0 ppm | TBD | 4.5 | TBD | 10 | 10 |
| Pure oxygen | — | 4.5 | 0.5 | 10 | 10 |
| Room air | — | 1.05 | 3.95 | 10 | 10 |

REFERENCES

The references listed below as well as all references cited in the specification, including patents, patent applications, and journal articles, are incorporated herein by reference to the extent that they supplement, explain, provide a background for, or teach methodology, techniques, and/or compositions employed herein.

Baumann et al. (1990) *Radiat Res* 123:325-30.
Bingle et al. (2002) *J Pathol* 196:254-265.
Boon et al. (1994) *Annu Rev Immunol* 12:337-365.
Braun et al. (1999) *Am J Physiol* 277:H551-H568.
Chaux et al. (1999) *J Immunol* 163:2928-2936.
Comerford et al. (2002) *Cancer Res* 62:3387-3394.
Dachs & Tozer (2000) *Eur J Cancer* 36:1649-1660.
Dejam et al. (2005) *Blood* 106:734-9.
Dewhirst et al. (1996) *Br J Cancer Suppl* 27:S241-S246.
Dewhirst et al. (1999) *Br J Cancer* 79:1717-1722.
Dolmans et al. (2003) *Nat Rev Cancer* 3:380-387.
Dorr et al. (1997) *Cancer Chemotherapy Handbook*, 2d edition, Appleton & Lange, Stamford, Conn., United States of America.
Dunn et al. (1999) *Br J. Cancer.* 80:117-126.
Feron (2004) *Trends Pharmacol Sci* 25:536-542.
Gaugler et al. (1994) *J Exp Med* 179:921-930.
Godelaine et al. (2003) *J Immunol* 171:4893-4897.
Goldstein (1996) *Eur J Cancer* 32A: 1039-1050.
Hamilton et al. (2002) *Cancer Treat Res* 112:67-87.
Hilf et al. (1965) *Cancer Res* 25:286-299.
Hill et al. (1996) *Br J Cancer Suppl* 27:S260-S263.
Horsman & Overgaard (2002) *In Basic Clinical Radiobiology*, Steel (ed.), Arnold, London, United Kingdom, pp. 156-168.

Kagan et al. (2001) *Cancer Res* 61:7777-7784.
Kimura et al. (1996) *Cancer Res* 56:5522-5528.
Kinoshita et al. (2001) *Intl J Cancer* 91:322-326.
Kufe et al. (2003) *Cancer Medicine*, BC Decker Inc., Hamilton, Ontario, Canada.
Le et al. (2005) *Proc Natl Acad Sci USA* 102:8758-63.
Leibel & Phillips (1998) *Textbook of Radiation Oncology*, Saunders, Philadelphia, United States of America.
Lewis & Murdoch (2005) *Am J Pathol* 167:627-635.
McMahon & Stamler (1999) *Methods Enzymol* 301:99-114.
McMillan & Steel (2002) *In Basic Clinical Radiobiology*, Steel (ed.), Arnold, London, United Kingdom, pp. 71-83.
Moeller et al. (2005) *Cancer Cell* 8:99-110.
Mueller-Klieser et al. (1983) *Br J Radiol* 56:559-564.
Mundt et al. (2000) *In Cancer Medicine*, Bast et al. (eds.), BC Decker Inc., Hamilton, Ontario, Canada.
Murdoch et al. (2004) *Blood* 104:2224-2234.
Paton et al. (2001) *J Physiol* 531, 445-458.
PCT International Patent Application Publications WO 94/05304; WO 94/16713; WO 95/25530; WO 95/33855; WO 96/29409; WO 98/32855; and WO 98/58956.
Peeters et al. (2004) *Intl J Cancer* 112:554-9.
Pittman (1995) *Microcirculation* 2:1-18.
Sorg et al. (2005) *J Biomed Opt* 10:44004.
Teicher et al. (1981) *Cancer Res* 41:73-81.
Teicher et al. (1985) *Intl J Cancer* 36:585-589.
Traversari et al., (1992) *J Exp Med* 176:1453-1457.
Tsai & Intaglietta (1993) *Intl J Microcirc Clin Exp* 12:75-88.
U.S. Patent Application Publication No. 2002/01336693.
U.S. Pat. Nos. 5,405,940; 5,462,871; 5,695,994; 6,034,214; 6,222,012; 6,314,956; 6,379,901; 6,488,932; and 6,676,855.
van Baren et al. (2005) *J Clin Oncol* 23:9008-9021.
Van den Eynde et al. (1995) *J Exp Med* 182:689-698.
van der Bruggen et al. (1994) *Eur J Immunol* 24:2134-2140.
Vaupel et al. (2001) *Semin Oncol* 28:29-35.
Yaromina et al. (2005) *Radiother Oncol* 76:206-12.
Zhong et al. (1999) *Cancer Res* 59:5830-5835.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of increasing perfusion in a hypoxic region of a cancer tissue or tumor in a subject, the method comprising administering to the subject:
   (a) a nitrosylated hemoglobin; and
   (b) a hyperoxic gas selected from the group consisting of pure oxygen and carbogen.

2. The method of claim 1, wherein the hemoglobin is present within a red blood cell that is administered to the subject.

3. A method of increasing perfusion in a hypoxic region of a tissue in a subject, the method comprising administering to the subject:
   (a) a composition comprising a nitrosylated hemoglobin; and
   (b) a hyperoxic gas,
   wherein the tissue comprises a tumor cell, a cancer cell, and combinations thereof.

4. The method of claim 1, wherein the subject is a mammal.

5. The method of claim 4, wherein the mammal is a human.

6. The method of claim 1, wherein the administering results in a $pO_2$ value in a plurality of cells of the hypoxic region of the tissue to at least about 10 mm Hg.

7. The method of claim 1, wherein the hypoxic region of the tissue results from a disease or disorder in the subject, and the administering ameliorates at least one symptom associated with the disease or disorder in the subject.

8. The method of claim 3, wherein the subject is a mammal.

9. The method of claim 8, wherein the mammal is a human.

10. The method of claim 3, wherein the administering results in a $pO_2$ value in a plurality of cells of the hypoxic region of the tissue to at least about 10 mm Hg.

11. The method of claim 3, wherein the hypoxic region of the tissue results from a disease or disorder in the subject, and the administering ameliorates at least one symptom associated with the disease or disorder in the subject.

* * * * *